(12) United States Patent
Tsien et al.

(10) Patent No.: US 6,686,458 B2
(45) Date of Patent: *Feb. 3, 2004

(54) SYNTHETIC MOLECULES THAT SPECIFICALLY REACT WITH TARGET SEQUENCES

(75) Inventors: Roger Y. Tsien, La Jolla, CA (US); B. Albert Griffin, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/126,752

(22) Filed: Apr. 19, 2002

(65) Prior Publication Data

US 2003/0083373 A1 May 1, 2003

Related U.S. Application Data

(63) Continuation of application No. 09/372,338, filed on Aug. 11, 1999, now Pat. No. 6,451,569, which is a continuation of application No. 08/955,859, filed on Oct. 21, 1997, now Pat. No. 6,008,378.

(51) Int. Cl.[7] .......................... A61K 49/00; A61K 51/00; C07F 9/70; C07F 9/80; C07H 21/00

(52) U.S. Cl. ..................... 536/23.1; 424/1.65; 424/1.85; 424/9.1; 424/9.36; 424/9.361; 424/9.42; 424/9.44; 424/9.6; 534/10; 534/16; 544/4; 544/64; 544/226; 546/3; 549/3; 549/39; 549/207; 556/30; 556/68; 556/70; 556/71; 556/72

(58) Field of Search ................................. 435/174, 188; 436/528, 529, 531, 532; 525/54.1; 530/344, 345, 391.1, 403, 404, 405, 406, 408, 409, 410, 412, 413, 415, 417, 300; 546/3; 548/402; 549/3, 39, 207, 305, 320; 568/306; 424/1.11, 1.65, 1.81, 1.85, 1.89, 9.1, 9.36, 9.361, 9.364, 9.365, 9.37, 9.42, 9.44, 9.6; 536/23.1; 534/10, 16; 544/4, 64, 226; 556/30, 68, 70, 71, 72

(56) References Cited

U.S. PATENT DOCUMENTS

| 5,932,474 A | * | 8/1999 | Tsien et al. | ............... 435/320.1 |
| 6,008,378 A | * | 12/1999 | Tsien et al. | ................. 549/207 |
| 6,054,271 A | * | 4/2000 | Tsien et al. | ..................... 435/6 |
| 6,451,569 B1 | * | 9/2002 | Tsien et al. | ................. 435/174 |

OTHER PUBLICATIONS

Belshaw et al., P.N.A.S. 93:4604–4607 (1996).
Berleth et al., J. Biol. Chem. 267:16403–16411 (1992).
Brown et al., Biochemistry. 26:863–871 (1987).
Brinkley, Bioconjugate Chem. 3:2–13 (1992).
Cubitt et al., TIBS. 20:448–455 (1995).
Cullen et al., J. Inorganic Biochemistry. 21:179–194 (1984).
Deerinck et al., J. Cell of Biol. 126:901–910 (1994).
Dill et al., Chem. Res. Toxicol. 2:181–185 (1989).
Dill et al., Magnetic Resonance in Chemistry. 251074–1077 (1987).
Dou, et al., J. Biol. Chem. 269:20410–20416 (1994).
Engel et al., Tetrahedron. 49:8761–8770 (1993).
Fancy, et al., Chemistry & Biology. 3:551–559 (1996).
Frost et al., J. Biol. Chem. 260:2646–2652 (1985).
Frost et al., Biochem. J. 269:589–595 (1990).
Ghadiri et al., J. Am. Chem. Soc. 112:1630–1632 (1990).

(List continued on next page.)

*Primary Examiner*—Jeffrey E. Russel
(74) *Attorney, Agent, or Firm*—Gray Cary Ware & Freidenrich, LLP; Lisa A. Haile; Kevin J. Forrestal

(57) ABSTRACT

The present invention features biarsenical molecules. Target sequences that specifically react with the biarsenical molecules are also included. The present invention also features kits that include biarsenical molecules and target sequences. Tetraarsenical molecules are also featured in the invention.

22 Claims, 12 Drawing Sheets

OTHER PUBLICATIONS

Ghadiri et al., J. Am. Chem. Soc. 112:9633–9635 (1990).
Gitler et al., Methods in Enzym. 233:403–415 (1994).
Hannestad, et al., Analyt. Biochem. 126:200–204 (1982).
Ho et al., Nature. 382:822–826 (1996).
Hoffman et al., J. Biol. Chem. 267:14005–14011 (1992).
Hoffman et al., Nucleic Acids Res. 19:6337–6338 (1991).
Jackson et al., J. Am. Chem. Soc. 113:9391–9392 (1991).
Kalef et al., Analyt. Biochem. 212:325–334 (1993).
Kalef et al., Methods in Enzym 233:395–403 (1994).
Kaplan et al., Protein Science. 6:399–406 (1997).
Li et al., Biochemistry. 34:139–147 (1995).
Loring et al., Mol. Brain. Res. 15:113–120 (1992).
Lu et al., J. Biol. Chem. 271:5059–5065 (1996).
Murphy et al., Current Biology. 7:11 (1997), pp. 870–876.
Pike et al., Euro. J. of Neuroscience. 4:1362–1368 (1992).
Rossant et al., J. of Neurochemistry. 62:1368–1374 (1994).
Ruan et al., J. Am. Chem. Soc. 112:9403–9404 (1990).
Sharrocks, Gene. 138:105–108 (1994).
Shi et al., J. Biol. Chem. 271:9291–9297 (1996).
Simons, Jr. et al., J. Biol. Chem. 265:1938–1945 (1990).
Smith et al., Gene. 67:31–40 (1988).
Smith J. Biol. Chem. 263:7211–7215 (1988).
Spencer et al., Current Biology. 7:839–847 (1996).
Spencer et al., Science. 262:1019–1024 (1993).
Stevenson et al., American Chemical Society. 17:2189–2192 (1978).
Tuchscherer et al., Pure & Appl. Chem. 68:2153:2162 (1996).
Voordouw et al., Eur. J. Biochem. 118:541–546 (1981).
Welsh et al., Current Biology. 8:617–622 (1997).
Whittaker et al., Biochem. J. 41:56–62 (1947).
TIBS. 20:285–288 (1995).

\* cited by examiner

TAUTOMERS:

(III)

(IV)

SALTS:

(IV)

(V)

ANHYDRIDES:

(VI)

(VII)

Biotin conjugate

Enzyme conjugate via ε-amino group of a lysine (VIII)

phosphorescence (in absence of $O_2$)
singlet oxygen generation with $O_2$

Ln = Tb, Eu: luminescence metal chelation spin label (electron paramagnetic resonance)

SEQUENCE LISTING

<160> NUMBER OF SEQ ID NOS: 7

<210> SEQ ID NO 1
<211> LENGTH: 17
<212> TYPE: PRT
<213> ORGANISM: Artificial Sequence
<220> FEATURE:
<223> OTHER INFORMATION: Target sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(17)
<223> OTHER INFORMATION: AMIDATION

<400> SEQUENCE: 1

```
Trp Glu Ala Ala Ala Arg Glu Ala Cys Cys Arg Glu Cys Cys Ala Arg
1               5                   10                  15

Ala
```

<210> SEQ ID NO 2
<211> LENGTH: 85
<212> TYPE: DNA
<213> ORGANISM: Artificial Sequence
<220> FEATURE:
<223> OTHER INFORMATION: PCR primer for target sequence

<400> SEQUENCE: 2

```
cggcaattct taggccctgg cgcagcactc cctgcagcag gcctccctgg cggcggcctc      60
ggccttgtac agctcgtcca tgccc                                           85
```

<210> SEQ ID NO 3
<211> LENGTH: 75
<212> TYPE: DNA
<213> ORGANISM: Artificial Sequence
<220> FEATURE:
<223> OTHER INFORMATION: PCR primer for mutated calmodulin

<400> SEQUENCE: 3

```
cgcggatccg ccaccatgca tgaccaactg acatgctgcc agatttgctg cttcaaagaa      60
gccttctcat tattc                                                      75
```

<210> SEQ ID NO 4
<211> LENGTH: 17
<212> TYPE: PRT
<213> ORGANISM: Artificial Sequence
<220> FEATURE:
<223> OTHER INFORMATION: Target sequence

<400> SEQUENCE: 4

```
Ala Glu Ala Ala Ala Arg Glu Ala Cys Cys Arg Glu Cys Cys Ala Arg
1               5                   10                  15

Ala
```

<210> SEQ ID NO 5
<211> LENGTH: 6
<212> TYPE: PRT
<213> ORGANISM: Artificial Sequence
<220> FEATURE:
<223> OTHER INFORMATION: Rich target sequence motif
<220> FEATURE:
<221> NAME/KEY: VARIANT
<222> LOCATION: (3)..(3)
<223> OTHER INFORMATION: Xaa is any Amino Acid
<220> FEATURE:
<221> NAME/KEY: VARIANT
<222> LOCATION: (4)..(4)
<223> OTHER INFORMATION: Xaa is any Amino Acid

<400> SEQUENCE: 5

```
Cys Cys Xaa Xaa Cys Cys
1               5
```

<210> SEQ ID NO 6
<211> LENGTH: 9
<212> TYPE: PRT
<213> ORGANISM: Xenopus

<400> SEQUENCE: 6

Thr Glu Glu Gln Ile Ala Glu Phe Lys

-continued

```
<210> SEQ ID NO 7
<211> LENGTH: 9
<212> TYPE: PRT
<213> ORGANISM: Artificial Sequence
<220> FEATURE:
<223> OTHER INFORMATION: N-terminal of mutated calmodulin (calmodulin+
      cys4)

<400> SEQUENCE: 7

Thr Cys Cys Gln Ile Cys Cys Phe Lys
1               5
```

SYNTHETIC MOLECULES THAT SPECIFICALLY REACT WITH TARGET SEQUENCES

This application is a continuation of and claims priority to U.S. application Ser. No. 09/372,338, filed Aug. 11, 1999, now U.S. Pat. No. 6,451,569, which is a continuation of U.S. application Ser. No. 08/955,859, now U.S. Pat. No. 6,008,378, filed Oct. 21, 1997, which are all incorporated herein by reference.

This invention was made with Government support under Grant No. NS27177, awarded by the National Institutes of Health. The Government has certain rights in this invention.

FIELD OF THE INVENTION

This invention relates to compositions and methods for labeling molecules, particularly small, synthetic molecules that can specifically react with target sequences.

BACKGROUND OF THE INVENTION

Many techniques in the biological sciences require attachment of labels to molecules, such as polypeptides. For example, the location of a polypeptide within a cell can be determined by attaching a fluorescent label to the polypeptide.

Traditionally, labeling has been accomplished by chemical modification of purified polypeptides. For example, the normal procedures for fluorescent labeling require that the polypeptide be covalently reacted in vitro with a fluorescent dye, then repurified to remove excess dye and/or any damaged polypeptide. Using this approach, problems of labeling stoichiometry and disruption of biological activity are often encountered. Furthermore, to study a chemically modified polypeptide within a cell, microinjection can be required. This can be tedious and cannot be performed on a large population of cells.

Thiol- and amine-reactive chemical labels exist and can be used to label polypeptides within a living cell. However, these chemical labels are promiscuous. Such labels cannot specifically react with a particular cysteine or lysine of a particular polypeptide within a living cell that has numerous other reactive thiol and amine groups.

A more recent method of intracellular labelling of polypeptides in living cells has involved genetically engineering fusion polypeptides that include green fluorescent protein (GFP) and a polypeptide of interest. However, GFP is limited in versatility because it cannot reversibly label the polypeptide. The ability to generate a wide range of specifically labeled molecules easily and reliably would be particularly useful.

SUMMARY OF THE INVENTION

In a first aspect, the invention features a biarsenical molecule of the following formula:

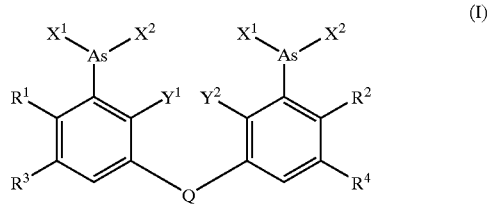

and tautomers, anhydrides, and salts thereof;

wherein:

each $X^1$ or $X^2$, independently, is Cl, Br, I, $OR^a$, or $SR^a$, or $X^1$ and $X^2$ together with the arsenic atom form a ring having the formula

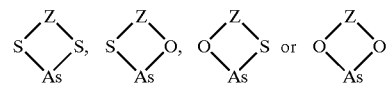

$R^a$ is H, $C_1$–$C_4$ alkyl, $CH_2CH_2OH$, $CH_2COOH$, or CN;

Z is 1,2-ethanediyl, 1,2-propanediyl, 2,3-butanediyl, 1,3-propanediyl, 1,2 benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis (carboxy)-1,2-ethanediyl;

$Y^1$ and $Y^2$, independently, are H or $CH_3$; or $Y^1$ and $Y^2$, together form a ring such that the biarsenical molecule has the formula

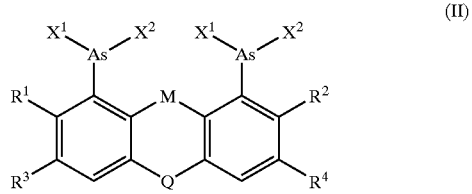

where M is O, S, $CH_2$, $C(CH_3)_2$, or NH;

$R^1$ and $R^2$, independently, are $OR^a$, OAc, $NR^aR^b$, or H;

$R^3$ and $R^4$, independently, are H, F, Cl, Br, I, $OR^a$, or $R^a$; or $R^1$ together with $R^3$, or $R^2$ together with $R^4$, or both, form a ring in which (i). one of $R^1$ or $R^3$ is $C_2$–$C_3$ alkyl and the other is $NR^a$ and (ii). one of $R^2$ and $R^4$ is $C_2$–$C_3$ alkyl and the other is $NR^a$;

$R^b$ is H, $C_1$–$C_4$ alkyl $CH_2CH_2OH$, $CH_2COOH$, or CN;

Q is $CR^aR^b$, $CR^aOR^b$, C=O, or a spirolactone having the formula:

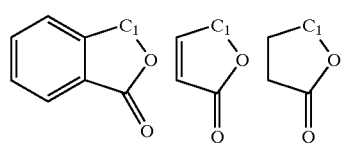

wherein the spiro linkage is formed at $C_1$.

Particularly preferred is a biarsenical molecule where $X^1$ and $X^2$ together with the arsenic atom form a ring having the formula

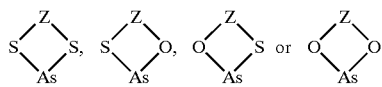

Also preferred is a biarsenical where $X^1$ and $X^2$ together with the arsenic atom form a ring having the formula

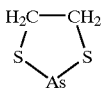

In another preferred embodiment of the biarsenical molecule, Q is chosen from the following spirolactones:

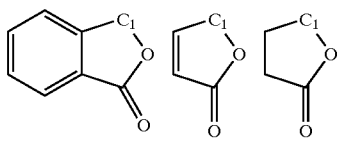

A more preferred embodiment is a biarsenical where Q is

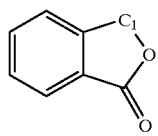

A particularly preferred biarsenical molecule has the following formula:

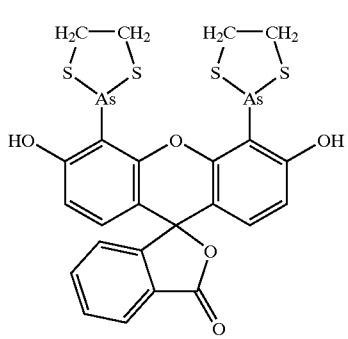

(III)

The tautomers, anhydrides and salts of the biarsenical molecule of formula (III) are also included.

Preferably, the biarsenical molecule specifically reacts with a target sequence to generate a detectable signal, for example, a fluorescent signal.

The biarsenical molecule preferably is capable of traversing a biological membrane. The biarsenical molecule preferable includes a detectable group, for example a fluorescent group, luminescent group, phosphorescent group, spin label, photosensitizer, photocleavable moiety, chelating center, heavy atom, radioactive isotope, isotope detectable by nuclear magnetic resonance, paramagnetic atom, and combinations thereof.

For some applications, the biarsenical molecule can be immobilized on a solid phase, preferably by covalent coupling.

In another aspect, the invention features a kit. The kit includes the above-described biarsenical molecule and a bonding partner that includes a target sequence. The target sequence includes one or more cysteines and is capable of specifically reacting with the biarsenical molecule. Preferably, the target sequence includes four cysteines. The target sequence preferably is a cys-cys-X-Y-cys-cys (SEQ ID NO:5) α-helical domain, where X and Y are amino acids. Preferably, X and Y are amino acids with high α-helical propensity. In some embodiments, X and Y are the same amino acids. In other embodiments, X and Y are different amino acids. In particularly preferred embodiments, the target sequence is SEQ ID NO. 1 or SEQ ID NO. 4.

The bonding partner can include a carrier molecule, for example a carrier polypeptide. In some embodiments, the target sequence is heterologous to the carrier polypeptide. In one preferred embodiment, the target sequence specified by SEQ ID NO. 4 is linked by a peptide bond to the carboxy terminal Lys-238 in the cyan mutant of the green fluorescent protein.

In yet another aspect, the invention features a kit that includes the above-described biarsenical molecule and a vector that includes a nucleic acid sequence encoding a target sequence. The target sequence includes one or more cysteines and is capable of specifically reacting with the biarsenical molecule. Preferably, the target sequence includes four cysteines.

In some preferred embodiments, the vector in the kit includes a nucleic acid sequence encoding a carrier polypeptide and a nucleic acid sequence encoding a target sequence. In some embodiments, the carrier polypeptide is heterologous to the target sequence.

In another aspect, the invention features a complex. The complex includes the above-described biarsenical molecule and a target sequence. In some preferred embodiments, the target sequence is SEQ ID NO. 1 or SEQ ID NO. 4. Preferably, the biarsenical molecule is biarsenical molecule of formula (III).

In another aspect, the invention features a tetraarsenical molecule. The tetraarsenical molecule includes two biarsenical molecules of the above-described formula. The two biarsenical molecules are coupled to each other through a linking group. In some embodiments, the tetraarsenical molecules have formula VI, VII, or VIII.

"Bonding partner" as used herein refers to a molecule that contains at least the target sequence.

"Heterologous" as used herein refers to two molecules that are not naturally associated with each other.

"Associated" as used herein includes association by covalent, as well as by non-covalent interactions.

The invention provides biarsenical molecules that can be engineered to exhibit a variety of properties. For example, the biarsenical molecule can be fluorescent. It can have different wavelengths of excitation and emission, e.g., visible or infrared. The biarsenical molecule specifically reacts with the cysteine-containing target sequence. In addition, the relatively small size of both the biarsenical molecule and the target sequence is particularly advantageous.

Other features and advantages of the invention will be apparent from the following detailed description and from the claims.

SEQUENCE ID NUMBERS

SEQ ID No. 1: acetyl-Trp-Glu-Ala-Ala-Ala-Arg-Glu-Ala-Cys-Cys-Arg-Glu-Cys-Cys-Ala-Arg-Ala-amide
Comments: The N-terminus is acetylated and the C-terminus is amidated.
SEQ ID No. 2: 5'-CGG CAA TTC TTA GGC CCT GGC GCA GCA CTC CCT GCA GCA GGC CTC CCT GGC GGC GGC CTC GGC CTT GTA CAG CTC GTC CAT GCC C-3'

SEQ ID No. 3: 5'-CGC GGA TCC GCC ACC ATG CAT GAC CAA CTG ACA TGC TGC CAG ATT TGC TGC TTC AAA GAA GCC TTC TCA TTA TTC-3'.

SEQ ID No. 4: Ala-Glu-Ala-Ala-Ala-Arg-Glu-Ala-Cys-Cys-Arg-Glu-Cys-Cys-Ala-Arg-Ala

DESCRIPTION OF THE PREFERRED EMBODIMENTS

Biarsenical Molecule

Figure 1:
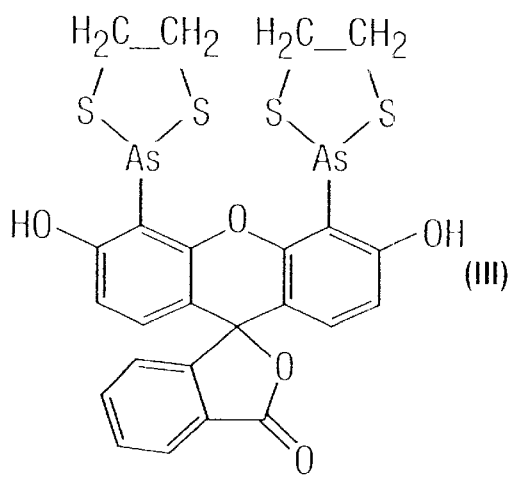
FIG. 1 illustrates pairs of biarsenical molecules that are tautomers, salts or anhydrides of each other.
Figure 1:
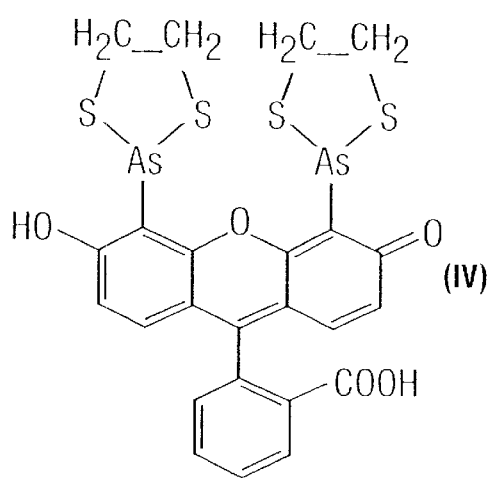
Figure 1:
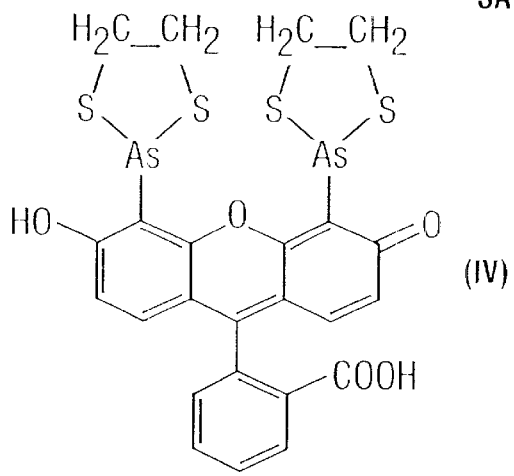
Figure 1:
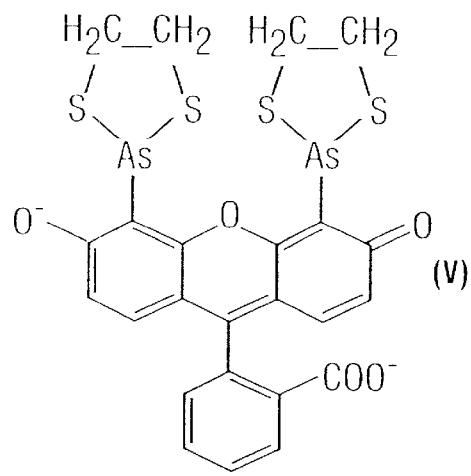
Figure 1:
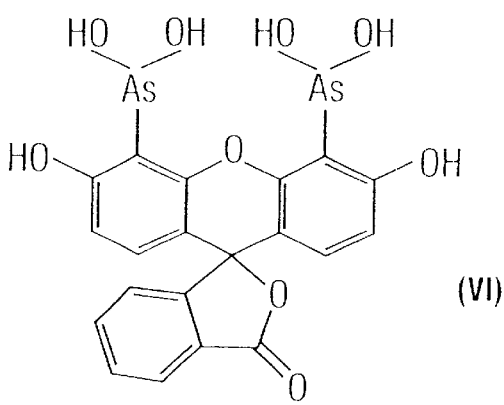
Figure 1:
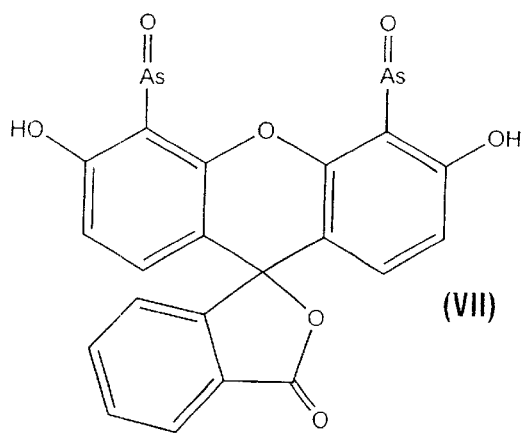

The invention provides biarsenical molecules having the formula described above in the Summary of the Invention. The present invention also includes tautomers, anhydrides and salts of the biarsenical molecule. FIG. 1 illustrates exemplary pairs of biarsenical molecules that are tautomers, anhydrides or salts of each other.

A number of dithiols may be used for bonding the arsenics. The dithiol groups may protect the biarsenical molecule from reacting with low affinity sites, for example, single cysteine residues or dihydrolipoic acid moieties. The dithiol may form a five- or six-membered ring with the arsenic. Vicinal dithiols that form five membered rings are preferable. Typically, the five-membered rings may be more stable. 1,3-dithiols forming six-membered rings may also be used.

The dithiol may contain additional substituents to control volatility, water solubility, proton ionization constants, redox potential, and tendency to complex with the arsenic. Increasing the molecular weight may decrease volatility and odor. Polar substituents such as hydroxymethyl, carboxyl and sulfo decrease volatility and increase water solubility. However, these substituents may also decrease the ability of the biarsenical molecule to traverse a biological membrane. Dithiols that contain rings may increase the affinity of the dithiol to the arsenic by organizing the two thiol groups to be in a cis-conformation ready to form an additional ring with the arsenic. Examples of dithiol rings are 1,2-benzenedithiol and 1,2-cyclohexanedithiol.

Preferably, each arsenic in the biarsenical molecule is bonded to a dithiol, such as 1,2-ethanedithiol (EDT). An unexpected advantage of the biarsenical molecule of formula (III) that is bonded to EDT is that it is essentially completely nonfluorescent. Biarsenical molecules that have detectable fluorescence are also within the scope of this invention.

"Q" in formula (I) is preferably a spirolactone. Particularly preferable is a biarsenical molecule in which Q is a bicyclic spirolactone as in formula (III). The tautomers, anhydrides and salts of molecule (III) are also within the scope of the invention.

The biarsenical molecule may be engineered to contain a variety of detectable groups. "Detectable group" as used herein refers to any atom or molecule that can be engineered into the biarsenical molecule to aid in the detection of the biarsenical molecule without significantly destroying the biarsenical molecule's ability to react with a target sequence.

Figure 6:
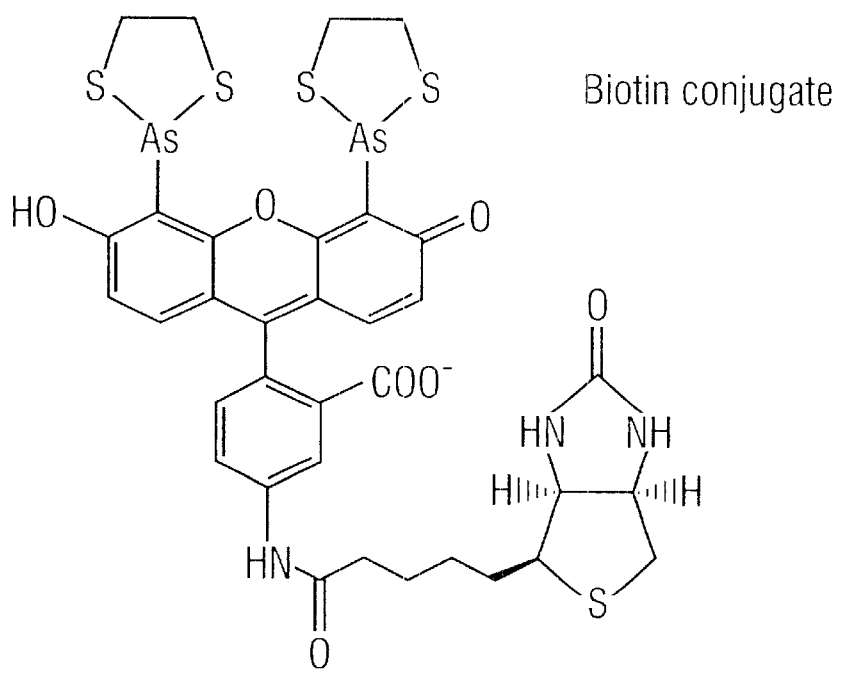
FIG. 6 illustrates biarsenical molecules with detectable groups.
Figure 6:
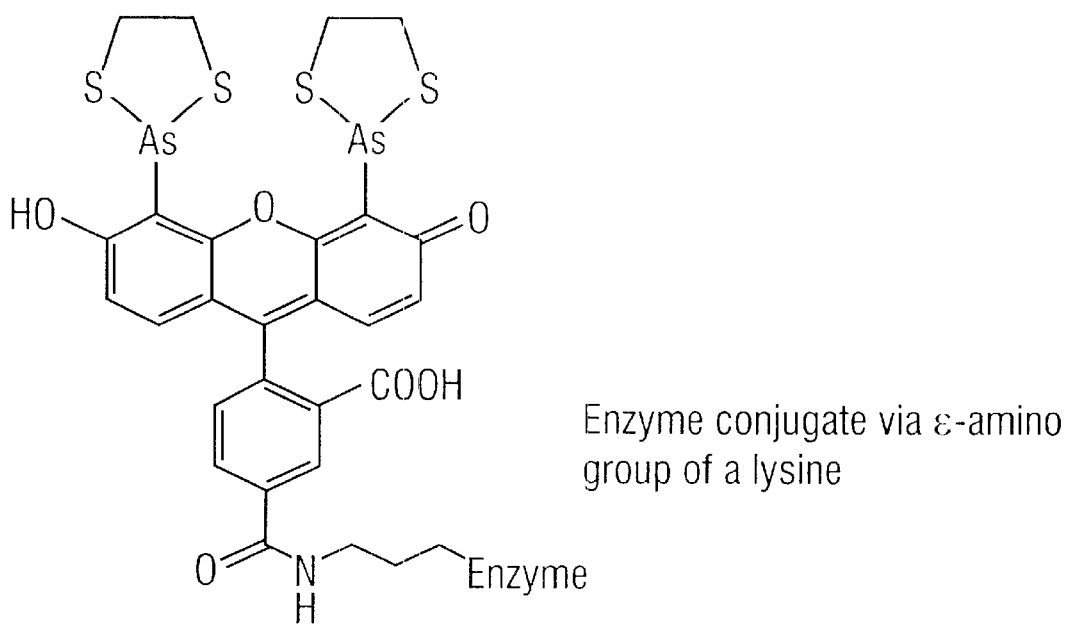
Figure 9:
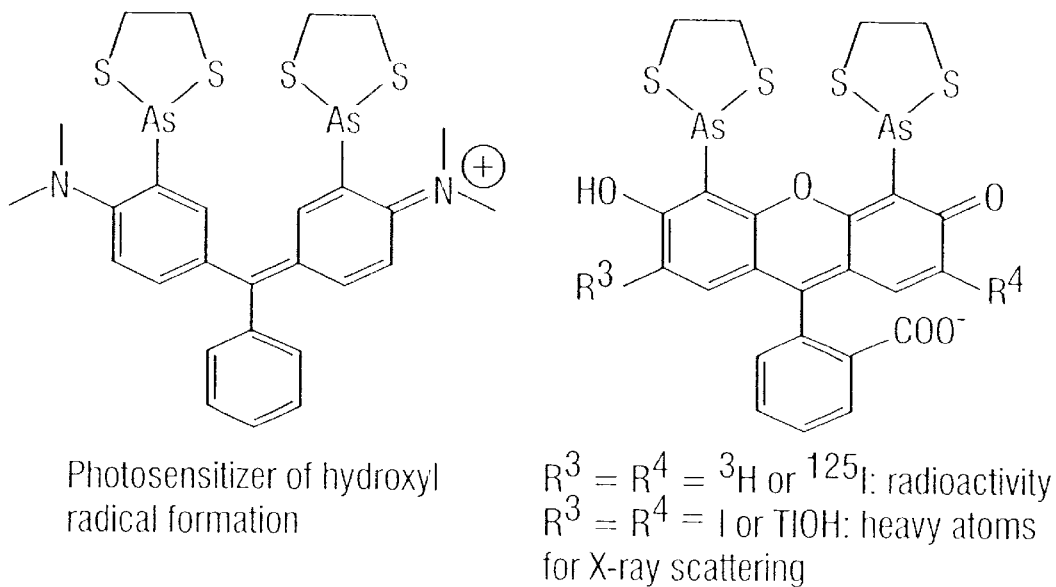
FIG. 9 illustrates biarsenical molecules with detectable groups.
Figure 9:
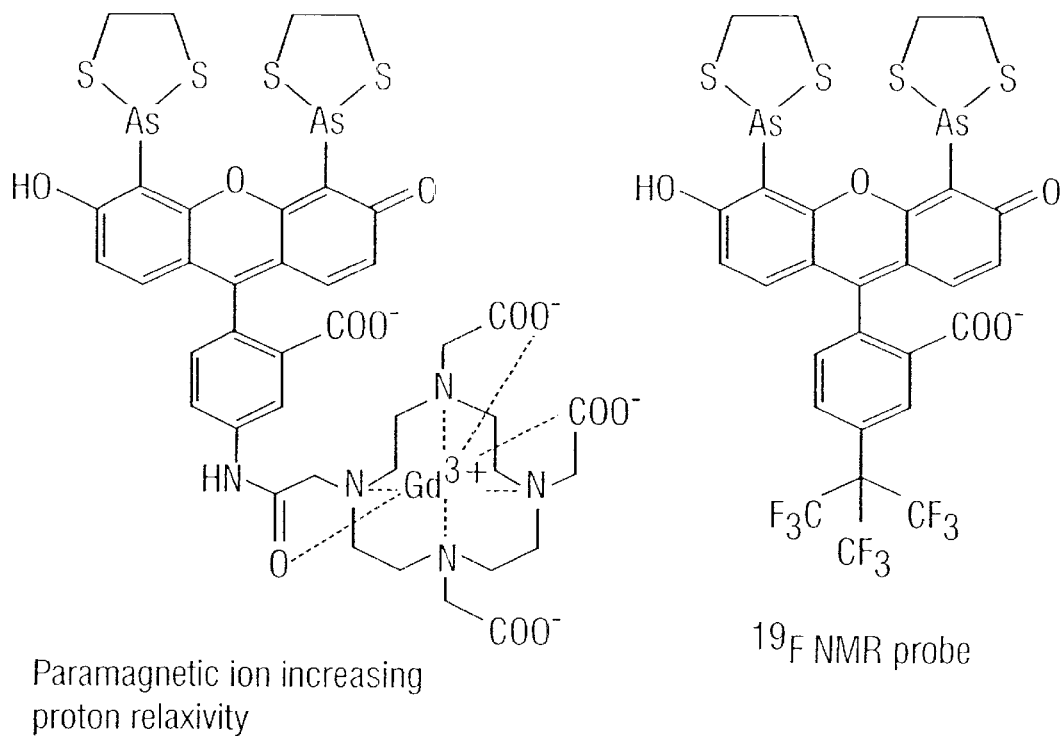
Figure 10:
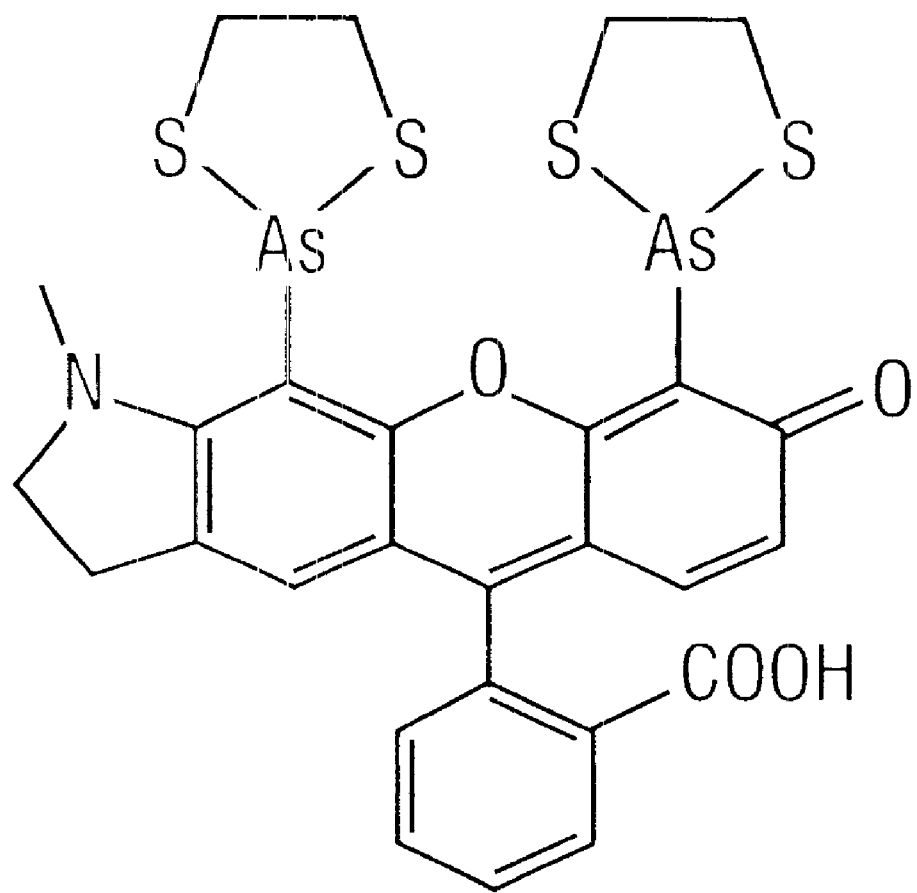
FIG. 10 illustrates a biarsenical molecule in which the fluorescent signal is sensitive to local solvent polarity.

The biarsenical molecule may be substituted at one or more positions to add a signal generating detectable group. Inclusion of more than one detectable group is also within the scope of this invention. The selection of a detectable group may be made based on the ease of the protocol for engineering the detectable group into the biarsenical molecule, and on the end use of the biarsenical molecule. Examples of detectable groups include fluorescent groups, phosphorescent groups, luminescent groups, spin labels, photosensitizers, photocleavable moieties, chelating centers, heavy atoms, radioactive isotopes, isotopes detectable by nuclear magnetic resonance, paramagnetic atoms, and combinations thereof. FIGS. 6, 8 and 9 illustrate biarsenical molecules with some of above-mentioned detectable groups. FIG. 10 illustrates a biarsenical molecule in which the fluorescent signal is sensitive to local solvent polarity.

Typically, a detectable group generates a detectable signal that can be readily monitored. Examples of detectable signals that can be monitored include fluorescence, fluorescence anisotropy, time-resolved luminescence, phosphorescence amplitude and anisotropy, electron spin resonance (ESR), singlet oxygen production, hydroxy radical-mediated protein inactivation, metal-ion sensing, X-ray scattering, radioactivity, nuclear magnetic resonance spectroscopy of the attached isotope, and enhanced relaxivity of protons in the immediate vicinity of a paramagnetic species.

Other modifying groups that aid in the use of the biarsenical molecule may also be incorporated. For example, the biarsenical molecule may be substituted at one or more positions to add a solid phase binding group or a cross-linking group. The biarsenical molecule may be coupled to a solid phase.

The biarsenical molecule preferably is capable of traversing a biological membrane. The small size of the biarsenical molecule can contribute toward the ability of the biarsenical molecule to traverse a biological membrane. Biarsenical molecules of less than 800 Daltons are preferable for membrane traversal.

The polarity of the biarsenical molecule can also determine the ability of the biarsenical molecule to traverse a biological membrane. Generally, a hydrophobic biarsenical molecule is more likely to traverse a biological membrane. The presence of polar groups can reduce the likelihood of a molecule to traverse a biological membrane. A biarsenical molecule that is unable to traverse a biological membrane may be derivatized. The biarsenical molecule may be derivatized by addition of groups that enable or enhance the ability of the biarsenical molecule to traverse a biological membrane. Preferably, such derivatization of the biarsenical molecule does not significantly alter the ability of the biarsenical molecule to subsequently react with the target sequence. The biarsenical molecule may also be derivatized transiently. In such instances, after traversing the membrane, the derivatizing group is eliminated to regenerate the original biarsenical molecule. Examples of derivatization methods that increase membrane traversability include esterification of phenols, ether formation with acyloxyalkyl groups, and reduction of chromophores to uncharged leuco compounds.

In some embodiments, the biarsenical molecule may be nearly or completely undetectable until it specifically reacts with a target sequence. The present inventors have surprisingly discovered that the biarsenical molecule (III) is non-fluorescent even though it is synthesized from a fluorescent molecule (parent fluorescein). The biarsenical molecule (III) specifically reacts with a target sequence to form a biarsenical molecule (III)/target sequence complex that is fluorescent. Moreover, the fluorescent signal generated by this complex is red-shifted by about 20 nm relative to fluorescein. This biarsenical molecule can be particularly useful because it provides a means to specifically and accurately detect the presence of the biarsenical molecule/target sequence complex with very little background signal.

Also within the scope of this invention is a biarsenical molecule that may be detectable before and after it specifically reacts with a target sequence to form the biarsenical molecule/target sequence complex. In such instances, it is preferable if the signal of the biarsenical molecule can be differentiated from the signal of the complex. For example, if the detectable signal of the biarsenical molecule is a fluorescent signal, it would be preferable if the fluorescence of the complex is red-shifted or blue-shifted relative to the biarsenical molecule alone.

The biarsenical molecule may also lack a detectable signal, both before and even after specifically reacting with a target sequence. These biarsenical molecules can be useful in many techniques that do not require a detectable signal, or that use other methods of detection. These biarsenical molecules may be useful when the goal is to attach a polypeptide to a solid substrate, cross-link two polypeptides or encourage a polypeptide domain to become α-helical.

Each of the two trivalent arsenics in the biarsenical molecule may react with a pair of adjacent cysteines. Thus, the biarsenical molecule may specifically react with four cysteines arranged in an appropriate configuration.

A particularly useful advantage of the specific reaction between the biarsenical molecule and a target sequence is the reversibility of the reaction. A complex containing the biarsenical molecule and the target sequence may be dissociated. Dissociation may be accomplished by providing an excess of reagents such as EDT as discussed in Example 2 below or other similar dithiols.

Figure 3:
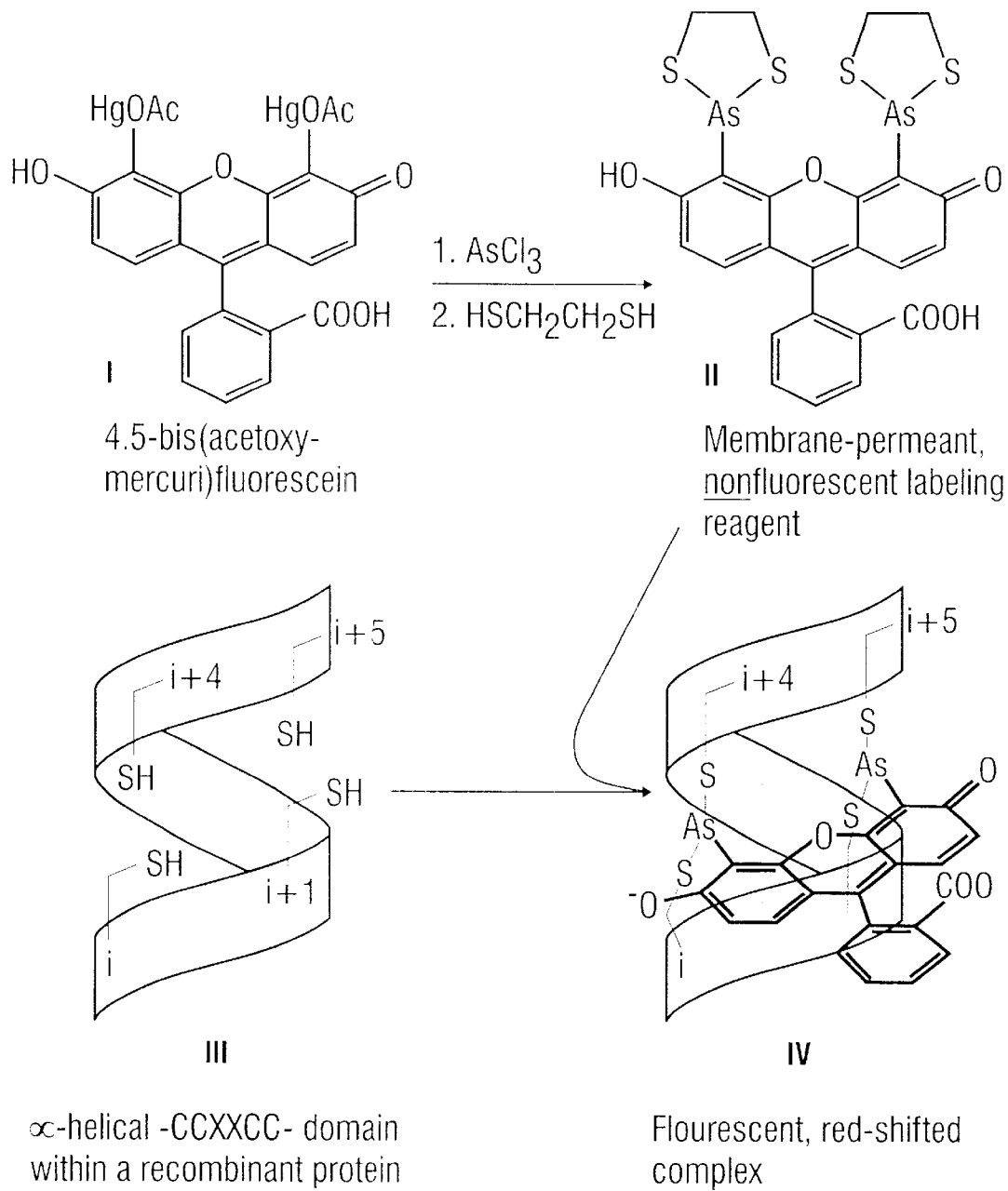
FIG. 3 is a reaction scheme showing the synthesis of the biarsenical molecule having formula (III). The figure also illustrates the specific reaction of the biarsenical molecule (III) with the target sequence.

In general, the biarsenical molecule can be prepared by a short synthesis. FIG. 3 shows the synthesis of the biarsenical molecule (III) from commercially available fluorescein mercuric acetate (FMA). Replacement of the two mercury atoms by arsenic can be catalyzed by palladium diacetate. The resulting 4',5'-bis-dichloroarsine fluorescein need not be isolated but may be coupled directly with EDT. Biarsenical molecule (III) can then be purified on silica gel.

Figure 2A:
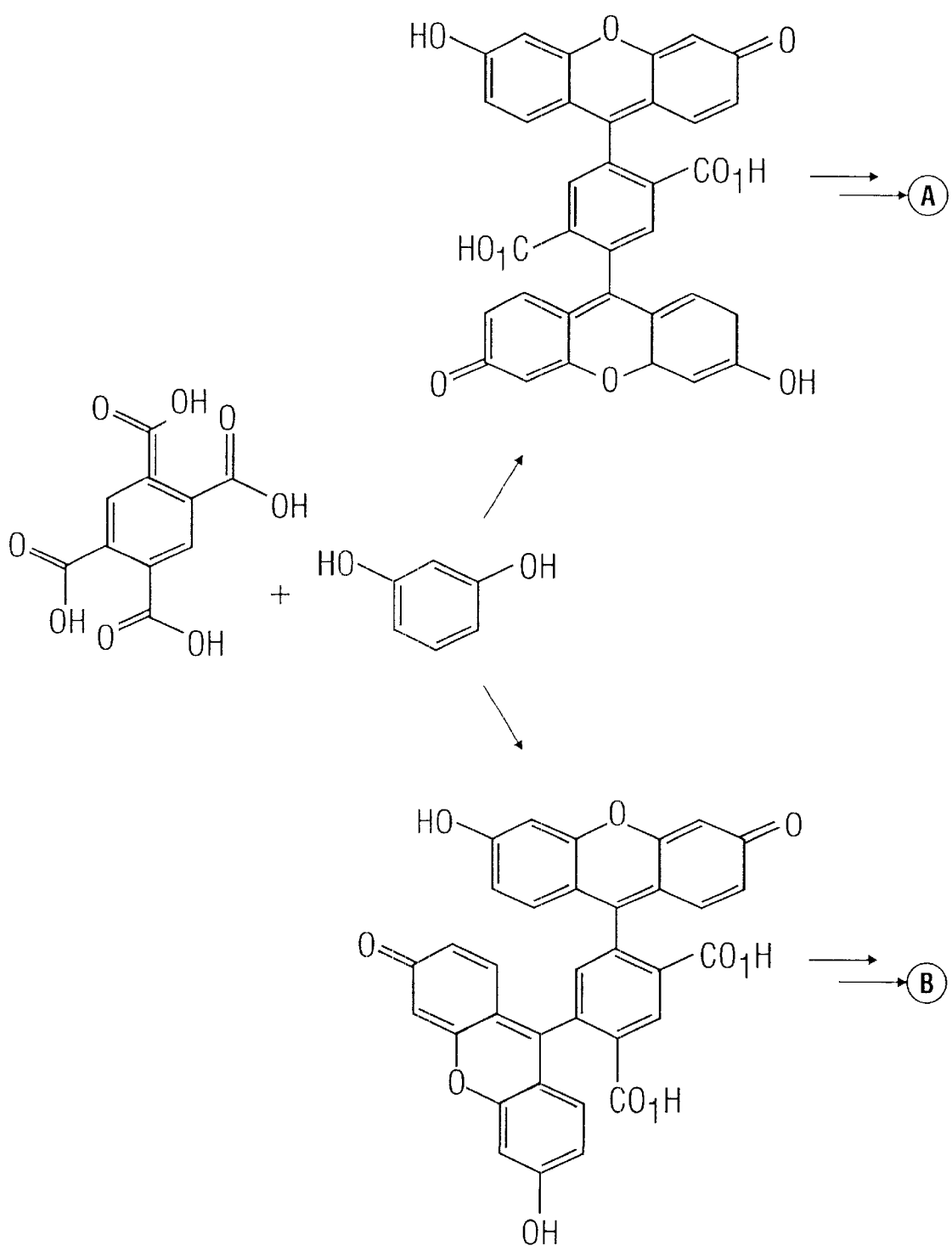
FIG. 2 is a reaction scheme for the synthesis of tetraarsenical molecules (VI) and (VII).
Figure 2B:
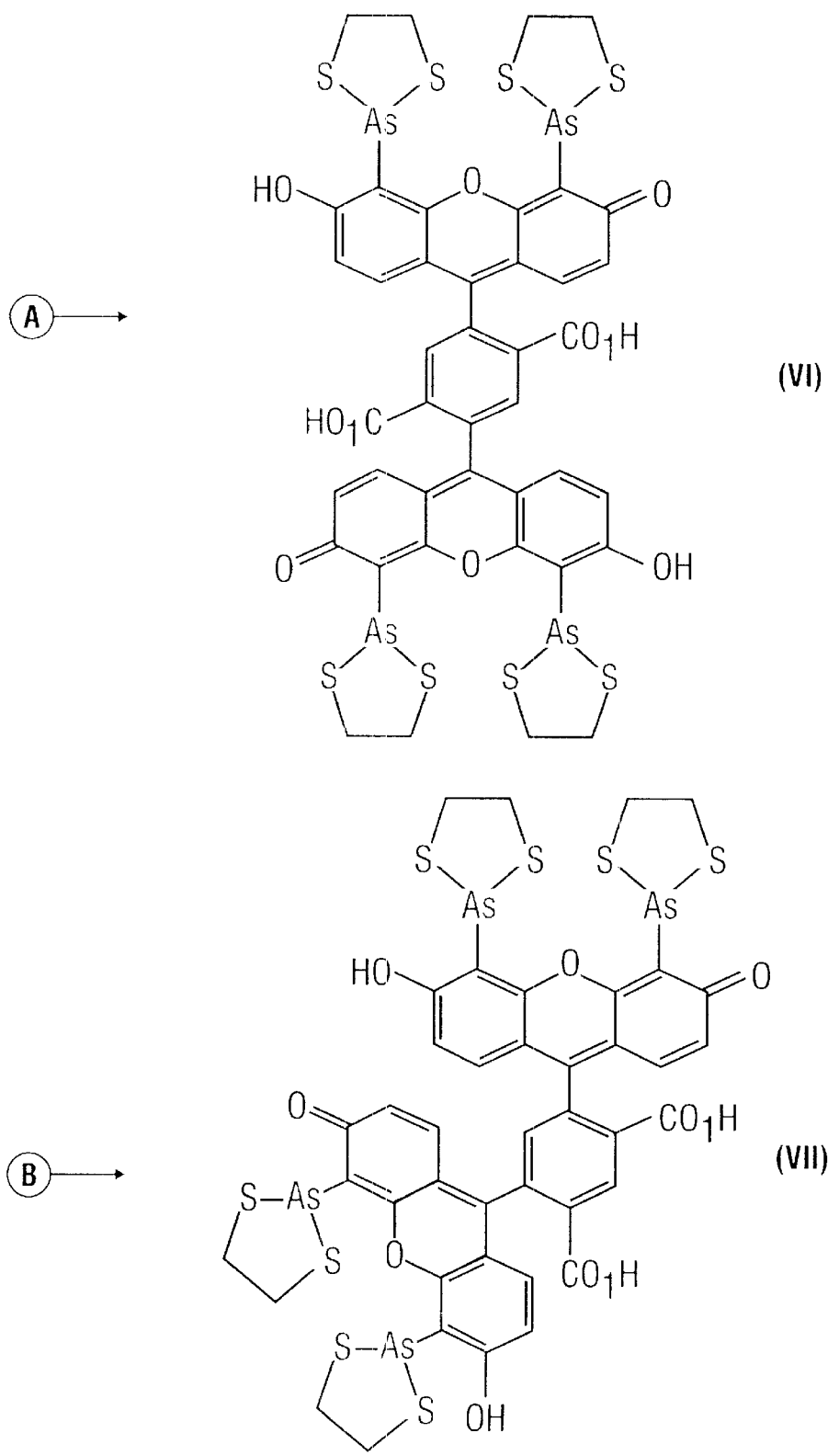
Figure 7:
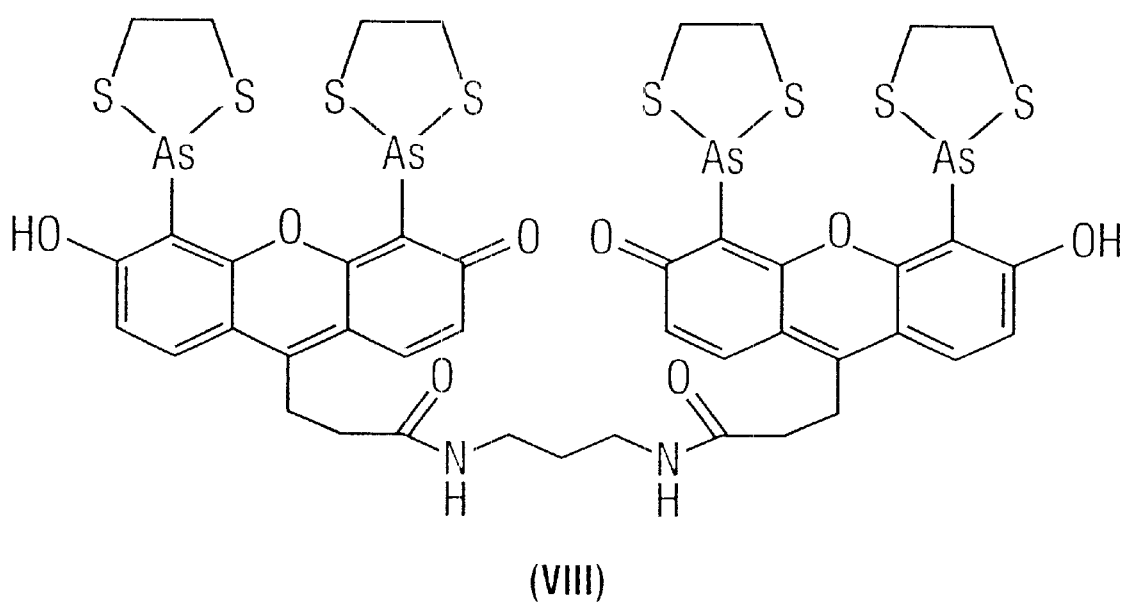
FIG. 7 illustrates the structure of a tetraarsenical molecule (VIII).
Figure 8A:
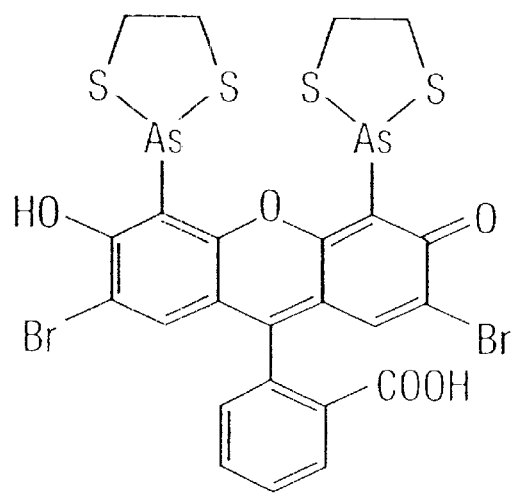
FIG. 8 illustrates biarsenical molecules with detectable groups.
Figure 8A:
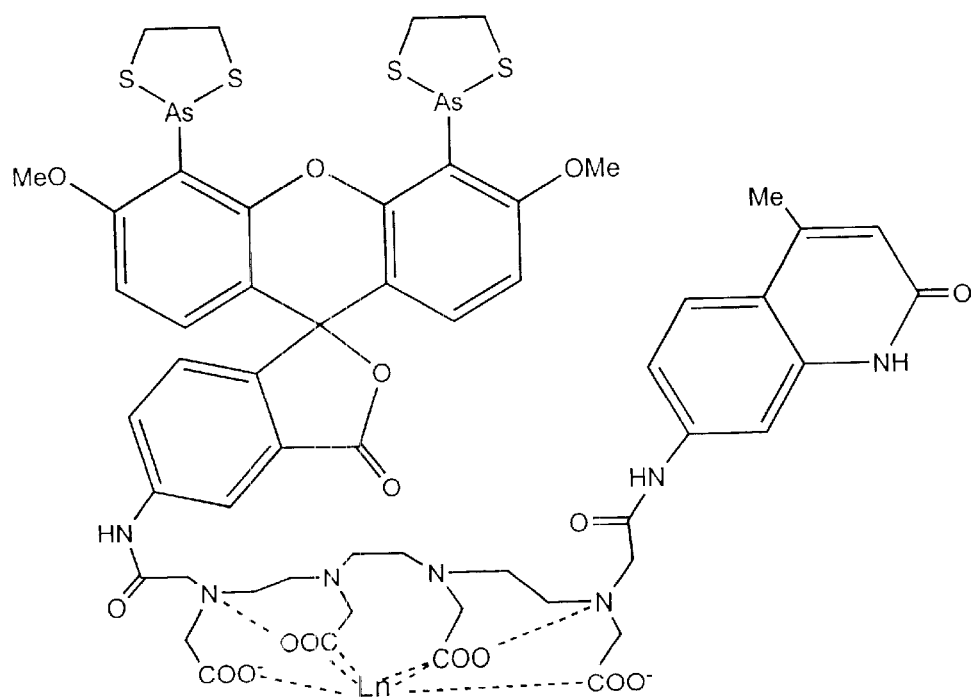
Figure 8B:
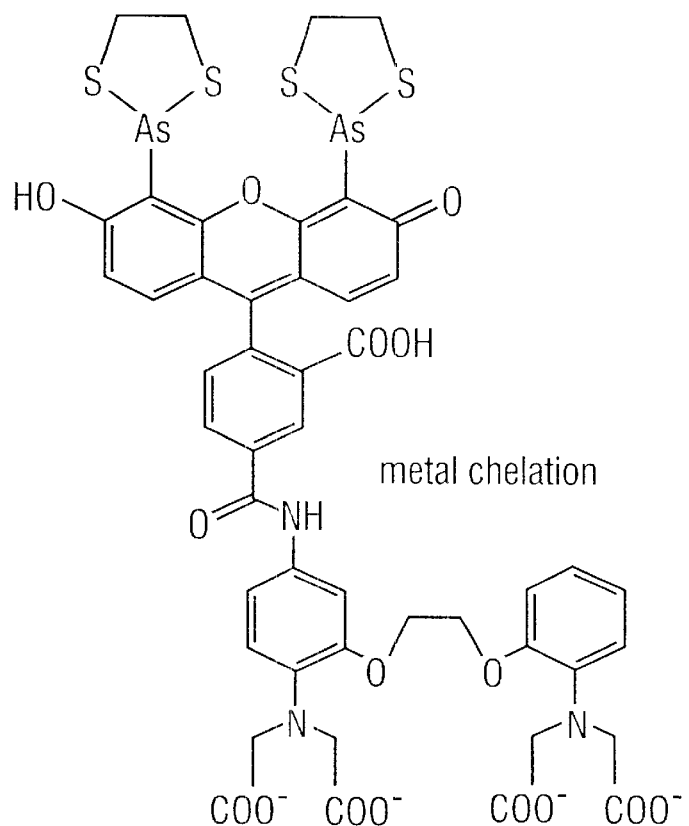
Figure 8B:
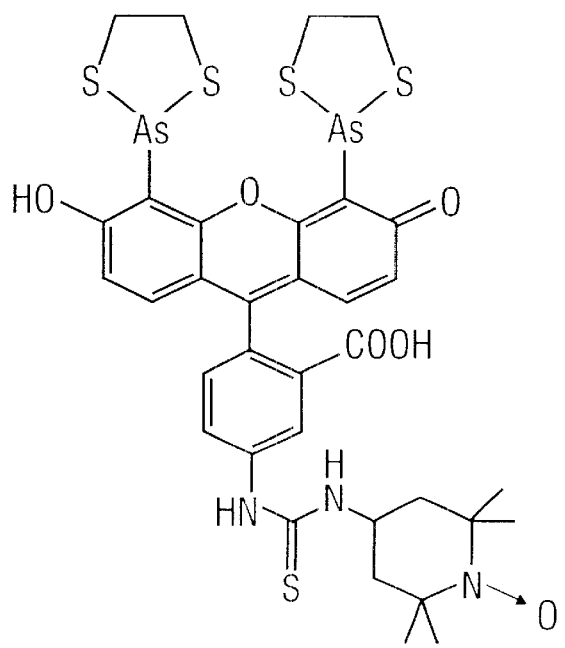

"Tetraarsenical" molecules as used herein refer to molecules that contain four arsenics. In some embodiments, tetraarsenical molecules are two biarsenical molecules chemically coupled to each other through a linking group. Tetraarsenical molecules may be synthesized in a variety of ways. FIG. 2 illustrates one scheme for synthesizing tetraarsenical molecules that have two biarsenical molecules coupled through either a para- or a meta- dicarboxylbenzene. The synthesis in FIG. 2 results in two types of molecules, a meta- and a para-substituted tetraarsenical molecule. FIG. 7 is another example of a tetraarsenical molecules coupled through a dialkylamido linking group. Other suitable linking groups include phenyl, naphthyl, and biphenyl groups. It follows that the tetraarsenical molecule can react with two target sequence. Tetraarsenical molecules may be particularly useful as cross-linking agents, e.g., intra-molecular and intermolecular cross-linking agents.

Target Sequence

Generally, the target sequence includes one or more cysteines, preferably four, that are in an appropriate configuration for reacting with the biarsenical molecule. The target sequence alone may be able to react with the biarsenical molecule. The target sequence can vary in size. Typically it contains at least 6 amino acids. Preferably, the target sequence is at least 10 amino acids. Alternatively, the target sequence may only adopt an appropriate configuration when it is associated with a carrier molecule. For example, the biarsenical molecule may react with a target sequence only when the target sequence is placed in an α-helical domain of a polypeptide.

The target sequence may have an amino acid sequence such that two pairs of cysteines are arranged to protrude from the same face of an α-helix. Preferably, the four sulfurs of the cysteines form a parallelogram.

The target sequence alone may not be completely helical under the reaction conditions. For example, reaction of a first arsenic with a pair of cysteines may nucleate an α-helix and position the two other cysteines favorably for reacting with the other arsenic of the biarsenical molecule.

The secondary structure of the target sequence may be an α-helix. An α-helical target sequence may include a primary amino acid sequence of cys-cys-X-Y-cys-cys (SEQ ID NO:5). The cysteines in this primary amino acid sequence are positioned for encouraging arsenic interaction across helical turns. The four cysteine residues of this sequence contain the sulfurs that specifically react with the biarsenical molecule. In this sequence, X and Y may be any amino acid, including cysteine. In some embodiments, X and Y may be the same amino acid and in other embodiments, S and Y may be different amino acids. The use of natural amino acids is preferable. Preferable amino acids at positions X and Y are amino acids with high α-helical propensity. Amino acids that have high α-helical propensity include alanine, leucine, methionine, and gluatmine.

Formation of an α-helix may also be favored by incorporation of oppositely charged amino acids that are separated by about three amino acids. These oppositely charged amino acids may be properly placed to form salt bridges across one turn of an α-helix. An example of a pair of oppositely charged amino acids is arginine and glutamate. Merutka & Stellwagen., *Biochemistry* 30: 1591–1594 and 4245–4248 (1991). It is preferable to position glutamate toward the N-terminus of the α-helix and arginine toward the C-terminus for favorable interaction with the dipole of an α-helix. The N-terminus of the target sequence may be acetylated. The C-terminus of the target sequence may be amidated.

A target sequence containing other secondary structures is also within the scope of this invention. For example, the one or more cysteines of the target sequence may be within a β-sheet structure. Other secondary structures are possible as long as the target sequence can react with the biarsenical molecule.

An example of a target sequence is SEQ ID NO. 1, as well as variants thereof that retain reactivity with the biarsenical molecule. In this target sequence, the N-terminus is acetylated and the C-terminus is amidated. A target sequence that is not acetylated and amidated at the N- and C-terminus is also within the scope of this invention. "Variant" target sequences contain one or more amino acid substitutions, typically with amino acid substitutes of approximately the same charge and polarity. Such substitutions can include, e.g., substitutions within the following groups: valine, isoleucine, leucine, methionine; aspartic acid, glutamic acid; asparagine, glutamine; serine, threonine; lysine, arginine; and phenylalanine, tyrosine. In general, such substitutions do not significantly affect the function of a polypeptide. Methods for producing target sequences include molecular biology methods and chemical polypeptide synthesis methods.

Bonding Partner

The bonding partner includes a cysteine-containing target sequence that specifically reacts with the biarsenical molecule. In addition to the target sequence, the bonding partner may also include a carrier molecule that is associated with the target sequence. Examples of carrier molecules include polypeptides, nucleic acids, sugars, carbohydrates, lipids, natural polymers, synthetic polymers, and other biologically or chemically active molecules.

Polypeptide Bonding Partner

In some embodiments, the carrier molecule can be a polypeptide. In such cases, the polypeptide is referred to as a carrier polypeptide. In these embodiments, the bonding partner includes the carrier polypeptide that is associated with the target sequence. A "polypeptide bonding partner" as used herein refers to a bonding partner that includes a carrier polypeptide and a target sequence. The carrier polypeptide can be any polypeptide of interest. Examples of carrier polypeptides include antibodies, receptors, hormones, enzymes, binding proteins, and fragments thereof.

The target sequence and the carrier polypeptide may be associated with each other covalently. Alternatively, the carrier polypeptide and the target sequence may be non-covalently associated.

The position of the target sequence with respect to the carrier polypeptide can vary in a bonding partner. The target sequence may be attached to the C-terminal end of the carrier polypeptide. Alternatively, the target sequence may be attached to the N-terminal end of the carrier polypeptide.

The target sequence may also be internal to the carrier polypeptide. An internal target sequence may be produced by inserting the target sequence at an internal site in the carrier polypeptide. Alternatively, an internal target sequence may be created by modifying one or more amino acids of the polypeptide to create a target sequence. Such internal sites are typically selected for their α-helical structures. Computer algorithms and x-ray crystallography data can be used to identify α-helical structures within polypeptides.

In some embodiments, the target sequence and the carrier polypeptide are heterologous to each other. The carrier polypeptide and the target sequence are also heterologous if the amino acid sequence of the carrier polypeptide is altered at one or more amino acid positions to generate the target sequence.

Any of the polypeptides and/or target sequences used in the invention, collectively referred to herein as "polypeptides", can be synthesized by such commonly used methods as t-BOC or FMOC protection of α-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Polypeptides may also be synthesized by the well known solid phase peptide synthesis methods described in Merrifield, (*J. Am. Chem. Soc.*, 85:2149, 1962), and Stewart and Young, *Solid Phase Peptides Synthesis*, (Freeman, San Francisco, 1969, pp. 27–62), using a copoly(styrene-divinylbenzene) containing 0.1–1.0 mMol amines/g polymer. On completion of chemical synthesis, the polypeptides can be deprotected and cleaved from the polymer by treatment with liquid HF-10% anisole for about ¼–1 hours at 0° C. After evaporation of the reagents, the polypeptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous polypeptide or polypeptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Polypeptides may also be produced by the "native chemical" ligation technique which links together polypeptides (Dawson et al., *Science*, 266:776, 1994). Protein sequencing, structure and modeling approaches for use with a number of the above techniques are disclosed in Protein Engineering, loc. cit., and Current Protocols in Molecular Biology, Vols. 1 & 2, supra.

The polypeptides can also be non-polypeptide compounds that mimic the specific reaction and function of a polypeptide ("mimetics"). Mimetics can be produced by the approach outlined in Saragovi et al., *Science*, 253:792–795 (1991). Mimetics are molecules which mimic elements of polypeptide secondary structure. See, for example, Johnson et al., "Peptide Turn Mimetics", in Biotechnology and Pharmacy, Pezzuto et al., Eds., (Chapman and Hall, New York 1993). The underlying rationale behind the use of peptide mimetics is that the peptide backbone exists chiefly to orient amino acid side chains in such a way as to facilitate molecular interactions. For the purposes of the present invention, appropriate mimetics can be considered to be the equivalent of any of the polypeptides used in the invention.

Vector

Useful polypeptides may also be generated by nucleic acid techniques involving expression of nucleic acid sequences that encode the polypeptides. The term "vector" refers to a plasmid, virus or other vehicle known in the art that has been manipulated by insertion or incorporation of a nucleic acid sequence.

Methods that are well known in the art can be used to construct vectors, including in vitro recombinant DNA techniques, synthetic techniques, and in vivo recombination/genetic techniques. (See, for example, the techniques described in Maniatis et al. 1989 Molecular Cloning A Laboratory Manual, Cold Spring Harbor Laboratory, N.Y.)

Suitable vectors include T7-based expression vectors for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. Retroviral vectors may also be used. Examples of retroviral vectors include Moloney murine leukemia virus, (MoMuLV), Harvey murine sarcoma virus (HaMuS-V), murine mammary tumor virus (MuMTV), and Rous Sarcoma Virus (RSV). Expression vectors suitable for in vitro expression may also be used.

Generally, the vector includes a nucleic acid sequence encoding the target sequence. Typically, the nucleic acid sequence is a DNA sequence, although the nucleic acid can be an RNA sequence. The nucleic acid sequence can be any sequence that encodes a target sequence capable of reaching with the biarsenical molecule. This can include nucleic acid sequences that are degenerate variants of each other. By "degenerate variants" is meant nucleic acid sequences that encode the same amino acid sequence, but in which at least one codon in the nucleotide sequence is different. Degenerate variants occur due to the degeneracy of the genetic code, whereby two or more different codons can encode the same amino acid. Nucleic acid sequences of the present invention may be synthetic.

The vector may also contain a nucleic acid sequence encoding a carrier polypeptide, in addition to the nucleic acid sequence encoding the target sequence. Nucleic acid sequences encoding the carrier polypeptide and the target sequence can form a recombinant gene that, when expressed, produces a polypeptide bonding partner.

The nucleic acid sequence encoding the target sequence can be on the 5' or 3'-end of the nucleic acid sequence encoding the carrier polypeptide. Alternatively, the nucleic acid sequence encoding the target sequence can be internal to the nucleic acid sequence encoding the carrier polypeptide. In such a case, the nucleic acid sequence encoding the target sequence can be spliced into an internal site of the nucleic acid sequence encoding the carrier polypeptide. In this case, the nucleic acid sequence encoding the target sequence is flanked by nucleic acid sequences encoding the carrier polypeptide.

The nucleic acid sequence encoding the carrier polypeptide may contain an appropriate restriction enzyme site within its nucleic acid sequence that can be used for inserting the nucleic acid sequence encoding the target sequence. Alternatively, an appropriate restriction enzyme site can be engineered in the nucleic acid sequence encoding the carrier polypeptide at a desired location. A restriction enzyme site may be engineered by any number of known methods.

The nucleic acid sequence encoding the carrier polypeptide may by altered at one or more positions to generate the nucleic acid sequence that encodes the target sequence. For example, calmodulin can be altered to create a target sequence as described in Example 3. In some embodiments, changes in the nucleic acid sequence encoding the carrier polypeptide may be made to generate a nucleic acid encoding a target sequence without substantially affecting the function of the carrier polypeptide.

Site-specific and region-directed mutagenesis techniques, as well as standard recombinant techniques can be employed for generating some of the nucleic acid sequences that encode the polypeptides used in the invention. See Current Protocols in Molecular Biology, Vol. 1, Ch. 8 (Ausubel et al., eds., J. Wiley & Sons 1989 & Supp. 1990–93); Protein Engineering (Oxender & Fox eds., A. Liss, Inc. 1987). In addition, linker-scanning and PCR-mediated techniques can be employed for mutagenesis. See PCR Technology (Erlich ed., Stockton Press 1989); Current Protocols in Molecular Biology, Vols. 1 & 2, supra.

The vector may also contain any number of regulatory elements for driving expression of the polypeptides. Nucleic acid sequences encoding polypeptides may be operatively associated with a regulatory element. Regulatory elements include, but are not limited to, inducible and non-inducible promoters, enhancers, operators and other elements that drive or otherwise regulate gene expression.

Typically, a nucleic acid sequence encoding a polypeptide is operatively linked to a promoter that is active in the appropriate environment, i.e. a host cell. A variety of appropriate promoters are known in the art and may be used in the present invention. The promoter may be a promoter that naturally drives expression of the carrier polypeptide. The promoter may be a viral promoter, a bacterial promoter, a yeast promoter, insect promoter or a plant promoter, and can be host cell-specific. Examples of promoters include, without limitation, T7, metallothionein I, or polyhedron promoters. For example, if the polypeptides will be expressed in a bacterial system, inducible promoters such as pL of bacteriophage gamma, plac, ptrp, ptac (trp-lac hybrid promoter) and the like may be used. In mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used.

The vector may also include enhancer sequences. Enhancer sequences can be placed in a variety of locations in relation to polypeptide-encoding nucleic acid sequences. For example, enhancer sequences can be placed upstream or downstream of the coding sequences, and can be located adjacent to, or at a distance from, the polypeptide encoding nucleic acid sequences.

The vector may also contain a nucleic acid sequence encoding a selectable marker for use in identifying host cells containing a vector. A selectable marker in a vector typically confers some form of drug or antibiotic resistance to the host cells carrying the vector.

A number of selection systems may be used. In bacterial host cells, a number of antibiotic markers may be used. Antibiotic markers include tetracycline, ampicillin, and kanamycin. In mammalian host cells, selections systems include, but are not limited to herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817). Also, antimetabolite resistance can be used as the basis of selection for dhfr, which confers resistance to methotrexate (Wigler, et al., 1980, Proc. Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78:2072; neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Additional selectable genes include, trpB, which allows cells to utilize indole in place of tryptophan; hisD, which allows cells to utilize histinol in place of histidine (Harman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Host Cell

A host cell may carry an exogenous bonding partner. "Exogenous" as used herein refers to any molecules that are introduced into a host cell. In preferred embodiments, the exogenous bonding partner is a polypeptide bonding partner.

A "host cell" can be any cell capable of carrying an exogenous bonding partner. Examples of host cells include bacterial cells, yeast cells, insect cells, mammalian cells, and plant cells. A suitable host cell type includes a cell of the following types: HeLa cells, NIH 3T3 (Murine), Mv 1 lu (Mink), BS-C-1 (African Green Monkey) and human embryonic kidney (HEK) 293 cells. Such cells are described, for example, in the Cell Line Catalog of the American Type Culture Collection (ATCC). Cells that can stably maintain a vector may be particularly advantageous. See, for example, Ausubel et al., *Introduction of DNA Into Mammalian Cells*, in Current Protocols in Molecular Biology, sections 9.5.1–9.5.6 (John Wiley & Sons, Inc. 1995). Preferably, host cells do not naturally express polypeptides containing target sequences that react with molecules of the invention.

An exogenous bonding partner can be introduced into a host cell by a variety of appropriate techniques. These techniques include microinjection of bonding partners and expression within a cell of nucleic acids that encode bonding partners.

A host cell can be manipulated to carry an exogenous bonding partner by introducing a nucleic acid sequence that, when expressed, produces the bonding partner. Any of the vectors described above containing a nucleic acid sequence encoding a bonding partner may be introduced into a host cell. A non-replicating nucleic acid molecule, such as a linear molecule that can express a bonding partner is also within the scope of this invention.

The expression of a desired nucleic acid molecule may occur through transient expression of the introduced polypeptide-encoding nucleic acid sequence. Alternatively, permanent expression may occur through integration of the introduced nucleic acid sequence into a host chromosome. Therefore the cells can be transformed stably or transiently. The term "host cell" may also include any progeny of a host cell. It is understood that all progeny may not be identical to the parental cell since there may be mutations that occur during replication. However, such progeny are included when the term "host cell" is used.

Typically, the vector that includes the nucleic acid sequence encoding the bonding partner is introduced into a host cell. Methods of stable transfer, meaning that the vector having the bonding partner encoding nucleic acid sequence is continuously maintained in the host, are known in the art. The vector, with appropriate regulatory elements for expression in a host cell, can be constructed as described above.

The vector may be introduced into a host cell by any conventional method, including retroviral transduction, electroporation, calcium phosphate co-precipitation, biolistics and liposome-based introduction. See, for example, Ausubel et al., *Introduction of DNA Into Mammalian Cells*, in CURRENT PROTOCOLS IN MOLECULAR BIOLOGY (John Wiley & Sons, Inc. 1995).

A variety of host cell-specific expression vector systems may be utilized to express polypeptides in a host cell. These include microorganisms such as bacteria transformed with recombinant bacteriophage DNA, plasmid DNA or cosmid DNA expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); or animal cell systems infected with recombinant virus expression vectors (e.g., retroviruses, adenovirus, vaccinia virus), or transformed animal cell systems engineered for stable expression. Polypeptides may require translational and/or post-translational modifications such as addition of carbohydrates. These modifications can be provided by a number of systems, e.g., mammalian, insect, yeast or plant expression systems.

Eukaryotic systems, and preferably mammalian expression systems, allow for proper post-translational modifications of expressed mammalian polypeptides to occur. Eukaryotic cells which possess the cellular machinery for proper processing of the primary transcript, glycosylation, phosphorylation, and advantageously, plasma membrane insertion of a polypeptide may be used as host cells.

Depending on the host cell and the vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology, 153:516–544) as described earlier. Selection of the appropriate transcription and translation elements are readily apparent to a person of ordinary skill in the art.

Vectors based on bovine papilloma virus which have the ability to replicate as extrachromosomal elements may be of particular interest (Sarver et al., 1981, Mol. Cell. Biol. 1:486). Shortly after entry of this DNA, the plasmid replicates to about 100 to 200 copies per cell. Transcription of the polypeptide encoding nucleic acid sequences does not require integration of the plasmid into the host's chromosome, thereby yielding a high level of expression. These vectors can be used for stable expression by including a selectable marker in the plasmid, such as, for example, the neo gene.

Factors of importance in selecting a particular expression system include: the ease with which a host cell that contains the vector may be recognized and selected from a host cell that does not contain the vector; the number of copies of the vector which are desired in a particular host cell; and whether it is desirable to be able to "shuttle" the vector between different types of host cells.

Uses of Biarsenical Molecules and Target Sequences

The biarsenical molecule, in combination with the target sequence, form a biarsenical molecule/target sequence complex that is useful in a number of methods. The complex is particularly useful in methods for labeling a carrier molecule. The carrier molecule can be associated with the target sequence to form a bonding partner. The bonding partner may be produced by any method, including a number of the above-described methods. In preferred embodiments, the carrier molecule is a polypeptide.

A bonding partner that includes a target sequence is contacted with the biarsenical molecule. Contact of the biarsenical molecule with the bonding partner is performed under conditions appropriate for a specific reaction to occur between the biarsenical molecule and the target sequence to form the biarsenical molecule/target sequence complex.

A biarsenical molecule/target sequence complex that generates a detectable signal may be used if detection of a labeled carrier molecule is desired. A particular advantage of using the biarsenical molecule and the target sequence for labeling is the specificity and the reversibility of the interaction. The biarsenical molecule/target sequence complex may be dissociated, for example, after the detection of the complex.

The biarsenical molecule may be added to a composition that includes the target sequence. The biarsenical molecule may or may not be capable of traversing a membrane. The bonding partner may be, for example, in a test tube, a microtiter well or immobilized on a solid phase. Uses of the biarsenical molecule/target sequence complex include polypeptide purification, immunoassays, and other biological and chemical assays.

Immobilization of either the biarsenical molecule or the bonding partner to a solid phase may be particularly useful. Immobilization may include adsorption, absorption or covalent bonding. A solid phase may be inert or it may be reactive for coupling. Solid phases that may be used include glass, ceramics, and natural or synthetic polymeric materials. Examples of polymeric materials include cellulose-based materials, dextran-based materials, and polystyrene-based materials.

The biarsenical molecule may be contacted with a bonding partner in a living cell. The bonding partner may be introduced into a cell or produced within a cell. A biarsenical molecule capable of traversing a biological membrane is preferable when the biarsenical molecule is introduced outside the cell and the bonding partner is inside the cell. Typically, a membrane traversing biarsenical molecule is preferable for use within a living cell. Examples of uses of the biarsenical molecule/target sequence complex within cells include polypeptide interactions, polypeptide location, polypeptide quantifications, nucleic acid molecule identification and location. One use of the biarsenical molecule of formula (III) in combination with the target sequence in HeLa cells is demonstrated in Example 2 below.

The biarsenical molecule may be used to induce a more favorable conformation of the bonding partner. For example, the bonding partner may have two possible conformations, but one of the conformations may be more functionally important. The bonding partner when it specifically reacts with the biarsenical molecule may adopt the more functionally important conformation. A functionally important conformation may be, for example, a conformation that can bind a drug.

A tetraarsenical molecule of the present invention can be used to cross-link two bonding partners. Each of the bonding partners includes a target sequence. In a preferred embodiment, each bonding partner contains a target sequence and a carrier molecule. The carrier molecule may be a polypeptide. The polypeptides in each of the bonding partners may be same. Alternatively, the polypeptides in each bonding partner may be different. The target sequences may be the same or they may be different in each bonding partner. For example, cross-linking of polypeptides may be valuable in studying the effects of polypeptide dimerization on signal transduction. Ho S. N., Biggar S. R., Spencer D. M., Schreiber S. L., and Crabtree G. R., *Nature* 382: 822–826 (1996); Spencer D. M., Wandless T. J., Schreiber S. L., and Crabtree G. R. *Science* 262: 1019–1024 (1993). The carrier polypeptide may be an enzyme or an antibody.

In some embodiments, a bonding partner containing the target sequence and an antibody as the carrier polypeptide may be cross-linked via a tetraarsenical molecule to a bonding partner containing the target sequence and an enzyme, as the carrier polypeptide. Such a composition may be useful, for example, in enzyme immunoassays.

A wide variety of assays exist that use detectable signals as a means to determine the presence or concentration of a particular molecule. Examples of such assays include immunoassays to detect antibodies or antigens, enzyme assays, chemical assays and nucleic acid assays. An above described biarsenical molecule/target sequence complex can be useful in these assays.

In general, assays may be performed as follows. A sample containing a molecule of interest associated with either the biarsenical molecule or the target sequence may be contacted with the target sequence or the biarsenical molecule, respectively. The resulting solution is then monitored for the presence of a detectable signal or a change in a detectable signal.

A particularly useful characteristic of the biarsenical molecule/target sequence complex is that the complex may be dissociated by adding an excess reagent such as EDT. The dissociation of the complex may be particularly useful in assays, polypeptide purification schemes, and within cells.

The invention will be further understood with reference to the following examples, which are purely exemplary, and should not be taken as limiting the true scope of the present invention as described in the claims.

EXAMPLES

Materials
Instruments:
UV-Vis: Cary 3E
Fluorimeter: Spex DM3000 fluorescence spectrometer with two SPEX 1681 0.22 m monochromators 450 W Xenon lamp.
Countercurrent: High speed counter current chromatograph (P.C. Inc.) with Shimadzu LC-8A preparative LC pump unit.
HPLC: Dionex Biol. C Column. Dionex Ionpac NSI (10-32) reverse phase.
NMR: Varian Gemini 200 MHz
Mass spectra: Hewlett-Packard 5989B electrospray mass spectrometer.
All reagents and solvents were purchased from Aldrich or Fisher and were used as received.

Example 1

Synthesis and Characterization of Biarsenical Molecule (III) and a Target Sequence Synthesis. A biarsenical molecule of formula (III) (4',5'-bis (2-arsa-1,3-dithiolan-2-yl)fluorescein), herein referred to as biarsenical molecule (III), was prepared by a short synthesis from commercially available fluorescein mercuric acetate (FMA). All of the steps were conducted at room temperature, unless otherwise indicated. FMA (72 mg, 85 $\mu$mol) was suspended in 1.5 mL dry N-methylpyrrolidinone under argon and dissolved to a pale yellow solution upon addition of 144 $\mu$l (1.7 mmol) of arsenic trichloride. A few grains of palladium diacetate and 120 $\mu$l dry diisopropylethylamine (DIEA) were added with stirring. After three hours, the reaction was added dropwise to a solution of 20 mL of 50% acetone:0.25 M phosphate buffer pH 7. 1,2-ethanedithiol (EDT) (285 $\mu$l, 3.4 mmol) was then added followed by chloroform (20 mL) after five minutes. After 20 minutes of stirring, the reaction mixture was diluted with 100 mL water and separated. The aqueous layer was extracted (2×20 mL) with chloroform. The combined chloroform layers were washed (1×25 mL) with 0.1 M $Na_2$EDTA pH 7, dried with $Na_2SO_4$ and evaporated. The resulting oil was dissolved in toluene (100 mL) and washed (3×25 mL) with water. After drying with $Na_2SO_4$ and evaporation, the product was purified by $SiO_2$ column chromatography, loaded in toluene and eluted with 10% ethylacetate-toluene. Trituration with 95% ethanol gave an orange-red solid. The yield was 21 mg (37%). $^1$H-NMR ($CDCl_3$ with a trace of $CD_3OD$) results were 2.3 (br s, 2+H, OH), 3.57 (m, 8H, —$SCH_2CH_2S$—) 6.60 (d, 2H, H-2' J=8.8 Hz), 6.69 (d, 2H, H-1' J=8.8 Hz), 7.19 (d, 1H, H-7), 7.66 (m, 2H, H-5,6), 8.03 (d, 1H, H-4).

Solutions of the material gave a single spot with thin layer chromatography (TLC) (ethylacetate-hexane 1:1, 0.1% acetic acid, $R_f$ 0.55), but on aging gave more polar material. Addition of a slight excess of EDT reversed this process suggesting some dissociation of the complex occurs with time. The extinction coefficient was 41,000 $M^{-1}cm^{-1}$ at 507.5 nm in 0.1 M KCl, 10 mM KMOPS, pH 7.3. In alkaline solution (pH 13), the extinction coefficient was 55,000 $M^{-1}cm^{-1}$ at 496.5 nm. Mass spectrum analysis indicated a molecular weight of 664.0 Da compared to the calculated molecular weight of 664.6 Da.

Target sequence synthesis. The crude polypeptide acetyl-Trp-Glu-Ala-Ala-Ala-Arg-Glu-Ala-Cys-Cys-Arg-Glu-Cys-Cys-Ala-Arg-Ala-amide (SEQ ID NO. 1), prepared by the UCSD peptide synthesis facility, was purified by counter current chromatography on a 390 mL planetary coil (PC, Inc.) revolving at 800 RPM using n-butanol as the stationary phase and water as the mobile phase (4 mL/min). The polypeptide eluted in a broad peak centered at 75 minutes after the water solvent front. This target sequence was used in the examples below unless otherwise indicated.

Formation of target sequence/biarsenical molecule (III) complex. Biarsenical molecule (III) (3 μl of 1 mM solution in DMSO) was added to 100 μl of 25 μM target sequence (SEQ. ID NO. 1) in 25 mM phosphate, pH 7.4, 100 mM KCl, 1 mM mercaptoethanesulfonate. After 1.5 hours, the reaction mixture (at room temperature) was injected onto a Dionex IonPac NS1 reverse phase HPLC column, gradient 20% to 46% acetonitrile (0.1% TFA) from 3 to 17 minutes. The complex eluted at 14.7 minutes (Free target sequence elutes at 12.6 minutes.) Mass spectrum analysis indicated a molecular weight of 2414.99 Da and the calculated molecular weight for the 1:1 complex was 2415.33 Da.

Quantum yield of target sequence/biarsenical molecule(III) complex. Solutions of fluorescein in 0.1 N NaOH and of target sequence/biarsenical molecule(III) complex in 25 mM phosphate, pH 7.4 and 100 mM KCl were adjusted to equal absorbances (0.0388) at 499 nm. The ratio of the integrated emission (excitation at 499 nm) of target sequence/biarsenical molecule(III) complex relative to fluorescein was multiplied by 0.9, the quantum yield of fluorescein, giving a quantum yield 0.44 for the target sequence/biarsenical molecule (III) complex.

Figure 4:
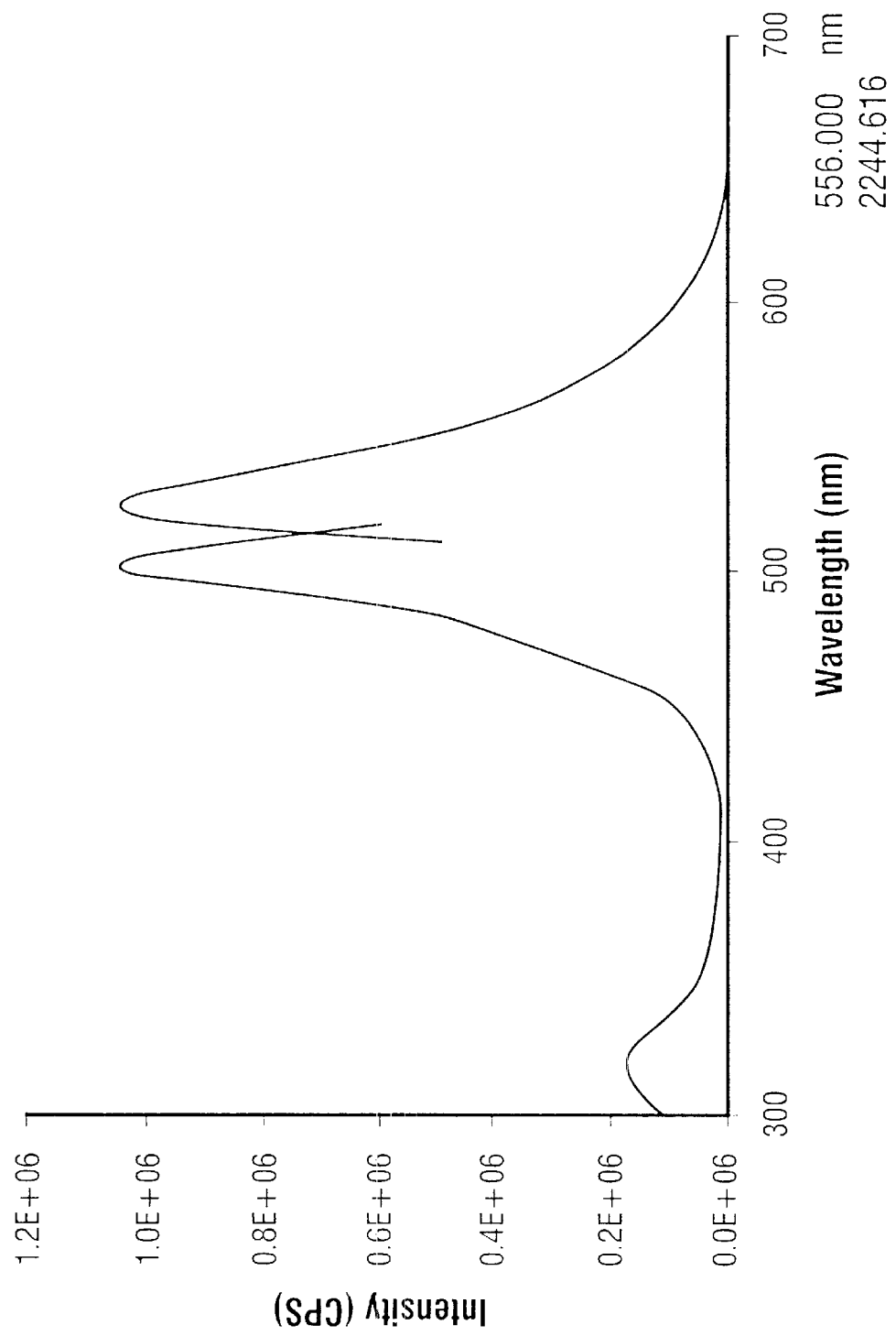
FIG. 4 is a plot of the excitation and emission spectra of the biarsenical molecule (III)/target sequence complex.

The biarsenical molecule (III) and the target sequence form a 1:1 complex as demonstrated by electrospray mass spectroscopy. This complex has a fluorescence quantum yield of 0.44 with excitation maximum at 508 nm and emission maximum at 528 nm (FIG. 4). The complex was of sufficient stability to remain intact in the presence of up to 100 equivalents of 2,3 dimercapto-1-propanol (BAL). Incubations with BAL were done at room temperature for 15 minutes. A 100 nM solution of the biarsenical molecule (III)/target sequence complex was barely affected by the addition of 1 μM or 10 μM BAL. Addition of 100 μM BAL resulted in a significant reduction in fluorescence, indicating that the biarsenical molecule (III)/target sequence complex was cleaved.

Monothiols were required for the efficient formation of the complex. That the monothiol is not functioning solely as a reducing agent was demonstrated by the fact that replacing the monothiol with triscarboxyethylphosphine does not result in efficient formation of the complex.

Example 2

The Use of Biarsenical Molecule (III) in Hela Cells

A polypeptide bonding partner that contains the target sequence (SEQ. ID NO. 4) attached to the cyan mutant of the green fluorescent protein was expressed in HeLa cells.

Expression of Cyan GFP-target sequence fusion in HeLa cells. Using standard molecular biology techniques, the target sequence (SEQ ID NO. 4) (with the tryptophan in SEQ ID NO. 1 replaced by an alanine) was attached to cyan fluorescent protein (CFP). CFP is the Green Fluorescent Protein (GFP) of *Aequorea victoria* with the following additional mutations: F64L, S65T, Y66W, N146I, M153T, V163A, N212K. Miyawaki A., et al. *Nature* 388:882–7 (1997). Fusion of the target sequence to the C-terminus of cyan GFP was accomplished using a PCR primer. The PCR primer had the following oligonucleotide sequence 5'-CGG CAA TTC TTA GGC CCT GGC GCA GCA CTC CCT GCA GCA GGC CTC CCT GGC GGC GGC CTC GGC CTT GTA CAG CTC GTC CAT GCC C-3' (SEQ ID NO. 2) encoding for the expression of the target sequence. It was inserted into the pcDNA3 vector (Invitrogen, Carlsbad, Calif.) using HindIII and EcoRl restriction sites. After amplification in DH5 bacteria, it was transfected (at 37° C.) into HeLa cells using the Lipofectin system from Gibco-BRL.

Measurement of FRET in HeLa cells. Three days after transfection, a concentration of 1.0 μM biarsenical molecule (III) and 10.0 μM ethanedithiol was applied to the transfected cells. Fluorescence changes were observed using a 440DF20 filter (Omega Optical, Brattleboro, Vt.) and a 4% transmittance neutral density filter for excitation and 480DF30 and 635DF50 filters for emission.

CFP is an engineered mutant of GFP with shorter wavelength excitation and emission maxima. It was chosen because its emission overlaps well with the excitation of biarsenical molecule (III)/target sequence fluorophore. The target sequence was fused to the C-terminus of CFP without additional linkers. The crystal structure of GFP shows that the final C-terminal amino acids are disordered and should thus provide enough flexibility to insure that the molecule (III)/target sequence fluorophore is not frozen in an unfavorable position for fluorescence resonance energy transfer (FRET).

Fluorescence changes were observed upon contacting cells with biarsenical molecule (III). A marker was used to indicate the cells that were expressing the target sequence and also to demonstrate that biarsenical molecule (III) was reacting with the target sequence in a specific manner. Fluorescence of the CFP indicated cells were expressing the target sequence and FRET between the CFP and biarsenical molecule (III)/target sequence demonstrated the specificity of the reaction.

Figure 5:
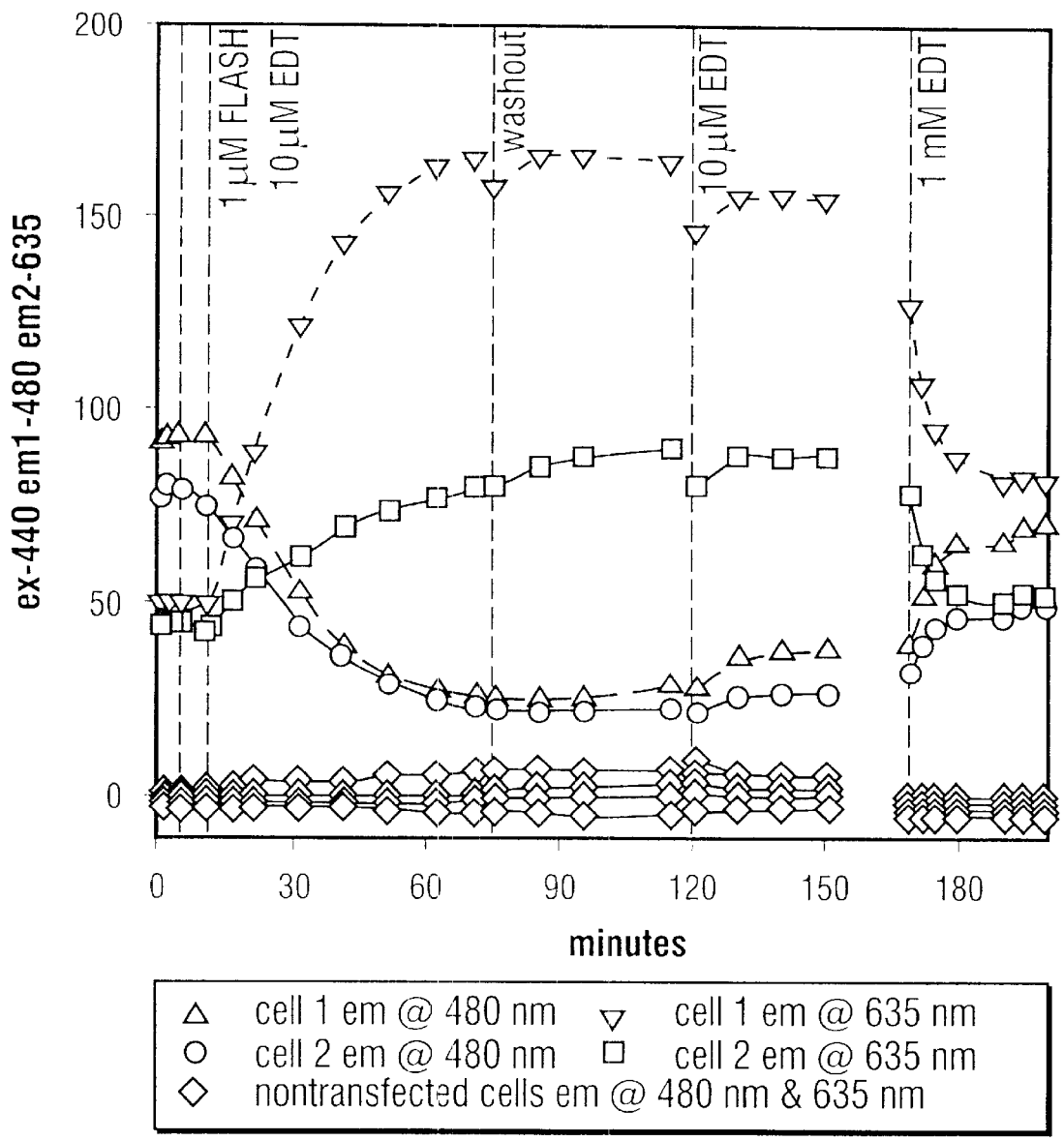
FIG. 5 is a plot of fluorescence intensity versus time in experiments with live HeLa cells. Hela cells were either nontransfected or transfected with the gene for the cyan mutant of green fluorescent protein fused to the target sequence. The HeLa cells were incubated with the biarsenical molecule (III).

HeLa cells expressing the fusion protein were contacted with biarsenical molecule (III) on a fluorescence microscope stage. Observed changes in fluorescence indicated that the desired specific reaction between the biarsenical molecule (III) and the target sequence had occured. FIG. 5 shows a time course of the fluorescence intensity for two cells at two different wavelengths (480 nm and 635 nm), corresponding to emission of CFP and the long-wavelength tail of the emission of biarsenical molecule (III)/target sequence, as well as traces for non-transfected cells in the same microscope field. At the start of the experiment, it can be seen that excitation of CFP resulted in emission mostly in the 480 nm channel. Upon addition of 1.0 μM biarsenical molecule (III) mixed with 10 μM EDT to inhibit background staining, the intensity of fluorescence at 480 nm decreased as energy was transferred from the CFP to the biarsenical molecule (III) which had reacted with the target sequence. There was a corresponding increase in fluorescence in the 635 nm channel due to biarsenical molecule (III)/target sequence emission. Upon removal of the biarsenical molecule (III)

solution, there was little change. Addition of 10 µM EDT resulted in only a small change.

Reversibility of the reaction was demonstrated by treating the cells with 1 mM EDT, a concentration sufficient to remove biarsenical molecule (III) from the target sequence in solution. However, the removal in cells was fast but not complete. Recovery of CFP fluorescence indicated that the former reduction of signal in this channel was indeed due to energy transfer and not to degradation of the CFP polypeptide.

An outstanding feature in this experiment was the absence of background fluorescence under the FRET conditions from either untransfected cells in the field or from the media containing biarsenical molecule (III). This was mostly due to the nonfluorescence of biarsenical molecule (III) in the presence of excess EDT. It was also helpful that in this experiment biarsenical molecule (III)/target sequence could only be excited by energy transfer as it had virtually zero excitation amplitude at 440 nm where CFP was illuminated.

In a separate experiment, conducted under the same conditions but different wavelengths, the signal at 535 nm was also investigated using an excitation at 480 nm, corresponding roughly to the spectra of biarsenical molecule (III)/target sequence. At these wavelengths, untransfected cells developed about 10% of the fluorescence of cells expressing the CFP-target sequence fusion, after subtraction of the signal from CFP that was present before application of biarsenical molecule (III). This level of background was low enough not to interfere with the use of biarsenical molecule (III) as a labeling reagent for many applications.

Example 3

Target Sequence Generated in Calmodulin

A target sequence that included the sequence Cys-Cys-X-Y-Cys-Cys (SEQ ID NO:5) was introduced into an existing helix in calmodulin. The crystal structure of calmodulin reveals an exposed α-helix where substitutions could be made without altering the amino acid residues responsible for calcium binding. In comparison, fusion of calmodulin (147 amino acids) to GFP (238 amino acids) would form a chimeric polypeptide more than two and a half times larger than calmodulin alone. Such a large increase in size might perturb the biological activity or localization of calmodulin.

Four cysteines were introduced into the N-terminal α-helix of xenopus calmodulin as shown below:

```
wild type:  5    6    7    8    9    10   11   12   13
            Thr  Glu  Glu  Gln  Ile  Ala  Glu  Phe  Lys  (SEQ ID NO:6)

—    —    Cys  Cys  —    —    Cys  Cys  —    —    (SEQ ID NO:7)
```

The mutated calmodulin is referred to as calmodulin+cys4. The substitutions were generated by using as a PCR primer of the following oligonucleotide sequence 5'-CGC GGA TCC GCC ACC ATG CAT GAC CAA CTG ACA TGC TGC CAG ATT TGC TGC TTC AAA GAA GCC TTC TCA TTA TTC-3' (SEQ ID NO. 3) encoding for the expression of these substitutions. The nucleic acid sequence encoding the cysteine-substituted calmodulin was inserted into pcDNA3 vector (Invitrogen, Carlsbad, Calif.) using the BamHI and EcoRI restriction sites. After amplification in DH5 bacteria, the vector was transfected (at 37° C.) into HeLa cells using the Lipofectin system from GibcoBRL.

Three days after transfection, the cells were treated with 1 µM biarsenical molecule (III) and 10.0 µM EDT for one hour. Observation on a fluorescence microscope stage using a 480DF30 filter (Omega Optical, Brattleboro, Vt.) and a 4% transmittance neutral density filter for excitation and a 535DF25 filter for emission revealed many cells with bright fluorescence compared to adjacent lightly stained cells. These lightly stained cells may have expressed the calmodulin+cys4 polypeptide, but at lower levels than the bright cells. Untransfected cells treated with the same concentrations of biarsenical molecule (III) and EDT had only very light fluorescence. Removal of the 1.4 neutral density filter was required to see details of the staining of the untransfected cells which appeared to be mitochondrial. This experiment demonstrated the feasibility of using biarsenical molecule (III) to label polypeptides within cells by creating a target sequence into already existing polypeptides, leaving the molecular weight of the polypeptide essentially unchanged.

Example 4

Synthesis of Dichloro Derivative of Biarsenical Molecule(III)

A solution of 84 mg (265 µmol) mercuric acetate in 500 µl 1:1 acetic acid/water was added (at room temperature) to a solution of 19 mg (47 µmol) of 2',7'-dichlorofluorescein in 500 µl ethanol. After stirring overnight, the red solid was filtered, rinsed with ether and dried under vacuum. 20 mg (22 µmol, 47%) of 2',7'-dichloro-4',5'-di(acetoxymercuri) fluorescein was collected.

The dichloro derivative of biarsenical molecule (III) (2', 7'-dichloro-4',5'-bis(2-arsa-1,3-dithiolan-2-yl)fluorescein) was prepared as follows. 2',7'-dichloro-4',5'-di (acetoxymercuri)fluorescein (13 mg, 14 µmol) was prepared as described above and suspended in 500 µl dry N-methylpyrrolidinone. Upon addition of 24 µl (285 µmol) arsenic trichloride, the suspended solid dissolved to a light yellow solution. DIEA (20 µl) and a catalytic amount of palladium diacetate were added. After three hours, the dark reaction mixture was quenched with 2.5 ml 1:1 acetone/water. EDT (200 µl) was added and the reaction stirred for 45 minutes. The product was extracted into chloroform. The organic layer was washed with saturated NaCl. Most of the solvent was removed by rotary evaporation and then additional chloroform was added. The white solid that precipitated was discarded. The product was isolated on silica gel with ethyl acetate-hexane 1:1,0.1% acetic acid as eluant. The retention factor, $R_f$, was 0.6 (1:1 ethyl acetate-hexane 1:1, 0.1% acetic acid). The yield was 113 mmole (1%) as determined by absorbance assuming a peak extinction coefficient of 80,000 $M^{-1}$ $cm^{-1}$.

Formation of a complex with target sequence and the dichloro-derivative of the biarsenical molecule (III). Dichloro-derivative of the biarsenical molecule (III) (5 µl of 675 µm solution in DMSO was added to 100 µl of 25 µM target sequence (SEQ ID NO. 1) in 25 mM phosphate, pH 7.4, 100 mM KCl 1 mM mercaptoethanesulfonate. After 1.5 hours, the reaction mixture was injected onto a Dionex IonPac SN1 reverse phase HPLC column, gradient 20% to 46% acetonitrile (0.1% TFA) from 3 to 17 minutes. The complex eluted in two overlapping peaks of the same molecular weight at 16.1 and 16.4 minutes. (Free peptide elutes at 12.6 minutes.) Mass spectrum analysis indicated a molecular weight of 2484.80 Da compared to the calculated molecular weight of the 1:1 complex was 2484.22 Da.

The dichloro-derivative of the biarsenical molecule (III) behaved similarly to the biarsenical molecule (III). A 10 nm red shift was obtained (excitation at 518 nm, emission at 538 nm).

Example 5

Synthesis of Tetraarsenical Molecules

Bifluorescein molecule. (See also O Silberrad (1906). *J. Chem. Soc.*, 89, 1787–1811 and S. Dutt (1926), *J. Chem. Soc.*, 1926, 1171–1184). Pyromellitic acid (744 mg, 2.93 mmol) and resorcinol (1.367 g, 12.4 mmol) were heated at 160° C. for two hours in the absence of solvent. After cooling to room temperature, the solid product was boiled in water and filtered. The orange solid that was collected was suspended in ethanol and filtered. 196 mg of crude product was precipitated upon addition of water to this filtrate. Two products giving closely spaced TLC spots ($R_f$=0.08 1:1 ethyl acetate/hexane) were isolated on silica gel with 99.9% ethyl acetate, 0.1% acetic acid. These most likely are the para- and meta-substitution isomers (FIG. 2). The orange solid (84 mg) containing the two isomers was collected (5%). Mass spectrum analysis indicated a molecular weight of 586.47 and the calculated molecular weight was 586.51.

Tetrakis(acetoxymercuri)bifluorescein. Mercuric acetate (252 mg, 790 μmol) dissolved in 2 mL 1:1 water/acetic acid was added to a mixture of 84 mg (143 μmol) bifluorescein in 6 ml ethanol. After stirring overnight, all material remained on baseline by TLC (1:1 ethylacetate/hexane) indicating that mercuration had occurred. The dark red solid (149 mg, 64%) collected by filtration was not further characterized.

Tetraarsenical molecules. The above material (67 mg, 41 μmol) suspended in 3 mL dry N-methylpyrrolidinone dissolved to a yellow solution upon addition of 140 μl (1.66 mmol) $AsCl_3$. DIEA (290 mL) and a catalytic amount of palladium diacetate were added. After 1.5 hours, the reaction was poured into a mixture of 5 mL acetone, 5 mL pH 7.4 phosphate buffer and 2 mL EDT. After removing the solvent from a chloroform extract of the aqueous reaction, the product was isolated on silica gel with 1:1 ethylacetate/hexane 0.1% acetic acid. Mass spectral analysis indicated a molecular weight of 1250.47 Da compared to a calculated molecular weight of 1250.86.

The final product isolated on silica was mostly of the correct mass (mass spectrum analysis indicated a molecular weight of 1250.47 and the calculated molecular weight was 1250.86). A small peak was also present corresponding to the mass of a product with one arsenic group missing (mass spectrum analysis indicated a molecular weight of 1084.55 and the calculated molecular weight was 1084.75.)

Formation of the tetraarsenical molecule complex with two target sequences. Tetraarsenical molecule (5 μl of 550 μM in DMSO) and 3 μl of 1.4 mM target sequence (SEQ ID NO. 1) were added to 50 μl 25 mM phosphate, pH 7.4, 100 mM KCl, 1 mM mercaptoethanesulphonate. After 1.5 hours, 10 μl of the reaction mixture was injected onto a C-18 reverse phase HPLC column linked to a mass spectrometer. A peak that eluted at 13 minutes contained a species with molecular weight of 4752.07 Da, compared to the calculated molecular weight for the 2:1 complex of 4752.11 Da, indicating that the desired complex had been formed.

Other embodiments are within the following claims. For example, the biarsenical molecule can have the following formula

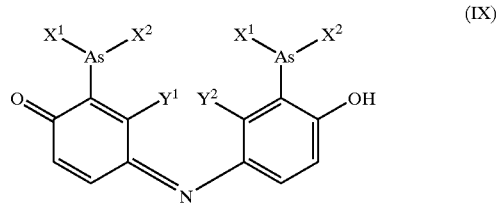

(IX)

One specific embodiment can have the following formula

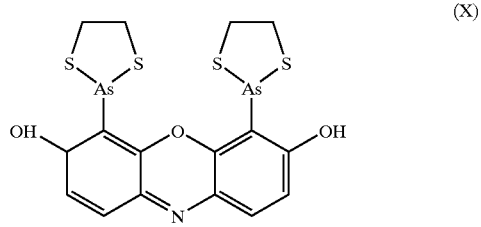

(X)

What is claimed is:

1. A biarsenical molecule of general formula:

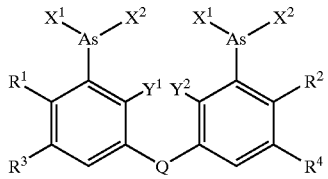

and tautomers, anhydrides, and salts thereof;
wherein
each $X^1$ or $X^2$, independently, is Cl, Br, I, $OR^a$, or $SR^a$, or
$X^1$ and $X^2$ together with the arsenic atom form a ring having the formula:

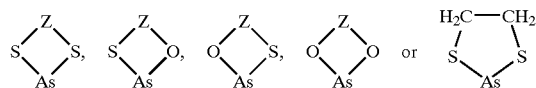

$R^a$ is H, $C_1$–$C_4$ alkyl, $CH_2$ $CH_2OH$, $CH_2COOH$ or CN;
Z is 1,2-ethanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;
$Y^1$ and $Y^2$, independently, are H or $CH_3$; or
$Y^1$ and $Y^2$, together form a ring such that the biarsenical molecule has the formula:

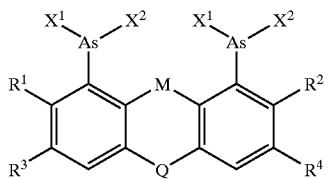

where M is O, S, $CH_2$, $C(CH_3)_2$, or NH;
$R^1$ and $R^2$, independently, are $OR^a$, OAc, $NR^aR^b$, or H;
$R^3$ and $R^4$, independently, are H, F, Cl, Br, I, $OR^a$, or $R^a$; or
$R^1$ together with $R^3$, or $R^2$ together with $R^4$, or both, form a ring in which
(i) one of $R^1$ or $R^3$ is $C_2$–$C_3$ alkyl and the other is $NR^a$ and
(ii) one of $R^2$ and $R^4$ is $C_2$–$C_3$ alkyl and the other is $NR^a$;

$R^b$ is H, $C_1$–$C_4$ alkyl, $CH_2CH_2OH$, $CH_2COOH$ or CN;
Q is $CR^aR^b$, $CR^aOR^b$, C=O, or a spirolactone having the formula:

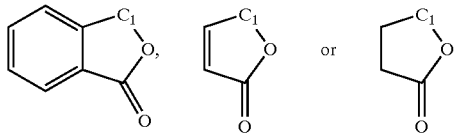

wherein the spiro linkage is formed at $C_1$, and wherein said molecule is substituted at one or more positions with a detectable group wherein said detectable group is selected from the group consisting of a fluorescent group, a luminescent group, spin label, photosensitizer group for singlet oxygen generation, photocleavable moiety, chelating center, heavy atom, radioactive isotope, isotope detectable by nuclear magnetic resonance and a paramagnetic atom.

2. The biarsenical molecule of claim 1, wherein said detectable group is a luminescent group.

3. A biarsenical molecule having a luminescent detectable group, wherein said biarsenical molecule has the following formula,

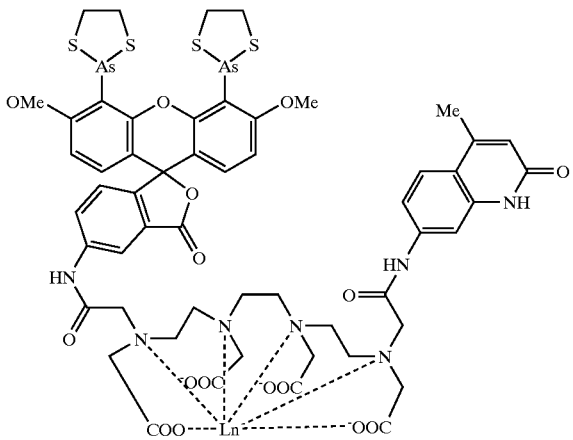

wherein Ln is Tb or Eu.

4. The biarsenical molecule of claim 1, wherein said detectable group is a photosensitizer group for singlet oxygen generation.

5. A biarsenical molecule comprising a detectable group comprising a photosensitizer group for singlet oxygen generation, wherein said biarsenical molecule has the following formula,

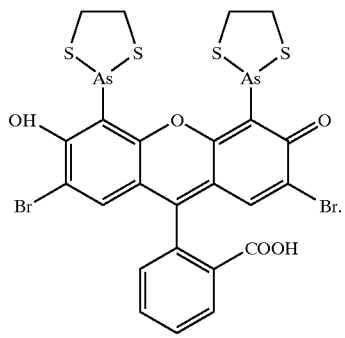

6. The biarsenical molecule of claim 1, wherein said detectable group is a chelating center.

7. A biarsenical molecule comprising a detectable group comprising a chelating center, wherein said biarsenical molecule has the following formula,

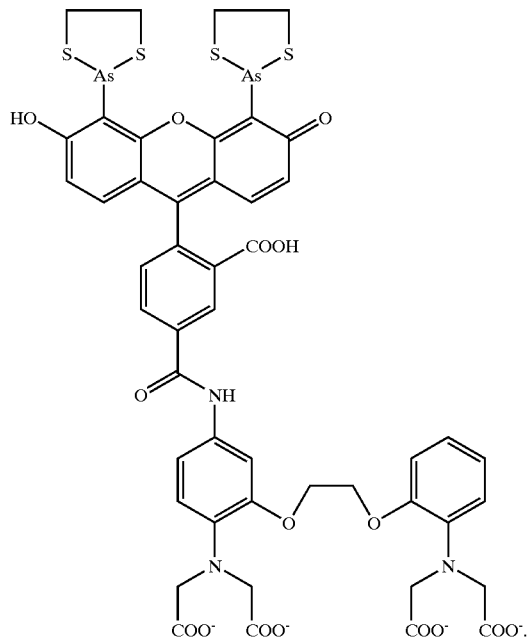

8. The biarsenical molecule of claim 1, wherein said detectable group is a heavy atom.

9. A biarsenical molecule comprising a detectable group comprising a heavy atom, wherein said biarsenical molecule has the following formula,

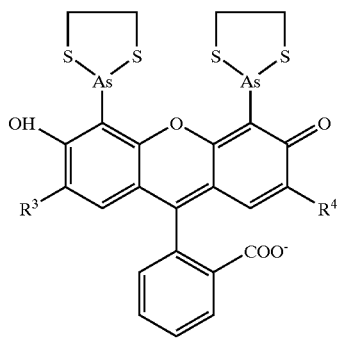

wherein $R^3=R^4=I$ or TlOH.

10. The biarsenical molecule of claim 1, wherein said detectable group is a radioactive isotope.

11. A biarsenical molecule comprising a detectable group comprising a radioactive isotope, wherein said biarsenical molecule has the following formula,

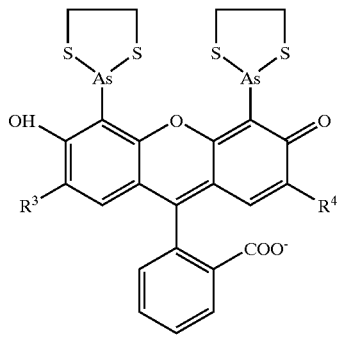

wherein $R^3=R^4={}^3H$ or ${}^{125}$-I.

12. The biarsenical molecule of claim 1, wherein said detectable group is an isotope detectable by nuclear magnetic resonance.

13. A biarsenical molecule comprising a detectable group comprising an isotope detectable by nuclear magnetic resonance, wherein said biarsenical molecule has the following formula,

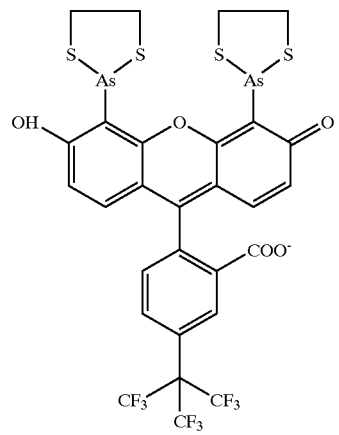

wherein F is ${}^{19}$F.

14. The biarsenical molecule of claim 1, wherein said detectable group is a paramagnetic atom.

15. A biarsenical molecule comprising a detectable group comprising a paramagnetic atom, wherein said biarsenical molecule has the following formula,

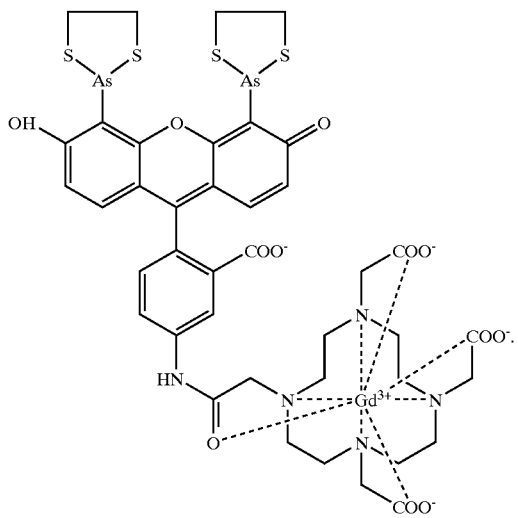

16. A biarsenical molecule of general formula,

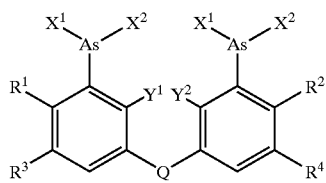

and tautomers, anhydrides, and salts thereof wherein
each $X^1$ or $X^2$, independently, is Cl, Br, I, $OR^a$, or $SR^a$, or
$X^1$ and $X^2$ together with the arsenic atom form a ring having the formula:

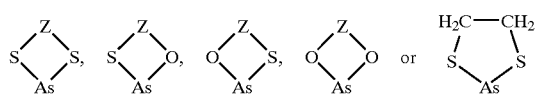

$R^a$ is H, $C_1$–$C_4$ alkyl, $CH_2$ $CH_2OH$, $CH_2COOH$ or CN;
Z is 1,2-ethanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;
$Y^1$ and $Y^2$, independently, are H or $CH_3$; or
$Y^1$ and $Y^2$, together form a ring such that the biarsenical molecule has the formula:

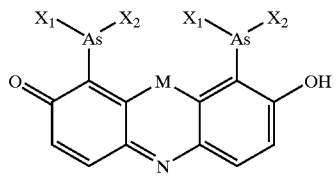

where M is O, S, $CH_2$, $C(CH_3)_2$, or NH.

17. The molecule of claim 16, wherein said $X^1$ and $X^2$ together with the arsenic atom form a ring having the formula,

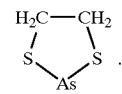

18. The molecule of claim 16, wherein said molecule is substituted at one or more positions with a detectable group.

19. The molecule of claim 16, wherein said molecule is fluorescent.

20. The biarsenical molecule of claim 16, wherein said biarsenical molecule has the following formula,

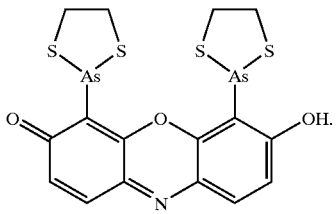

21. A kit comprising,
a) a biarsenical molecule comprising the following formula:

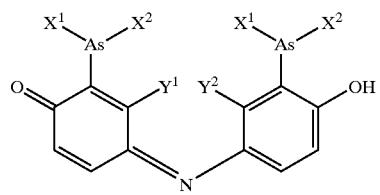

and tautomers, anhydrides, and salts thereof;
wherein
each $X^1$ or $X^2$, independently, is Cl, Br, I, $OR^a$, or $SR^a$, or
$X^1$ and $X^2$ together with the arsenic atom form a ring having the formula:

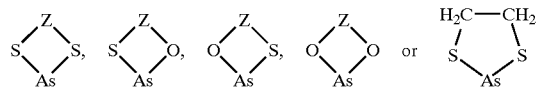

$R^a$ is H, $C_1$–$C_4$ alkyl, $CH_2$ $CH_2OH$, $CH_2COOH$ or CN;
Z is 1,2-ethanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;
$Y^1$ and $Y^2$, independently, are H or $CH_3$; or
$Y^1$ and $Y^2$, together form a ring such that the biarsenical molecule has the formula:

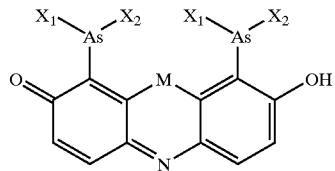

where M is O, S, $CH_2$, $C(CH_3)_2$, or NH, and b) a vector comprising a nucleic acid sequence encoding a target sequence, said target sequence comprising one or more cysteines capable of specifically reacting with said biarsenical molecule.

22. A kit comprising, a) a biarsenical molecule comprising the following formula:

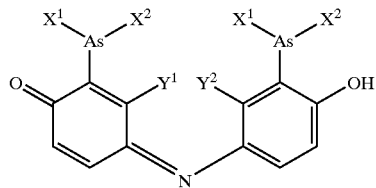

and tautomers, anhydrides, and salts thereof
wherein
each $X^1$ or $X^2$, independently, is Cl, Br, I, $OR^a$, or $SR^a$, or
$X^1$ and $X^2$ together with the arsenic atom form a ring having the formula:

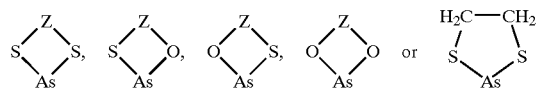

$R^a$ is H, $C_1$–$C_4$ alkyl, $CH_2$ $CH_2OH$, $CH_2COOH$ or CN;
Z is 1,2-ethanediyl, 1,2-benzenediyl, 4-methyl-1,2-benzenediyl, 1,2-cyclopentanediyl, 1,2-cyclohexanediyl, 3-hydroxy-1,2-propanediyl, 3-sulfo-1,2-propanediyl, or 1,2-bis(carboxy)-1,2-ethanediyl;
$Y^1$ and $Y^2$, independently, are H or $CH_3$; or
$Y^1$ and $Y^2$, together form a ring such that the biarsenical molecule has the formula:

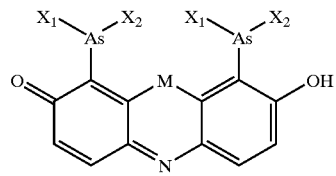

where M is O, S, $CH_2$, $C(CH_3)_2$, or NH, and b) a bonding partner.

* * * * *